US011001624B2

(12) United States Patent
Savvides et al.

(10) Patent No.: US 11,001,624 B2
(45) Date of Patent: May 11, 2021

(54) TSLP INHIBITORS

(71) Applicants: VIB VZW, Ghent (BE); UNIVERSITEIT GENT, Ghent (BE)

(72) Inventors: Savvas Savvides, Kortrijk (BE); Rudi Beyaert, Zingem (BE); Kenneth Verstraete, Ghent (BE); Harald Braun, Ghent (BE); Frank Peelman, Gentbrugge (BE)

(73) Assignees: VIB VZW, Ghent (BE); UniversiteitGent, Ghent (BE)

( * ) Notice: Subject to any disclaimer, the term of this patent is extended or adjusted under 35 U.S.C. 154(b) by 0 days.

(21) Appl. No.: 16/091,331

(22) PCT Filed: Apr. 4, 2017

(86) PCT No.: PCT/EP2017/057944
§ 371 (c)(1),
(2) Date: Oct. 4, 2018

(87) PCT Pub. No.: WO2017/174556
PCT Pub. Date: Oct. 12, 2017

(65) Prior Publication Data
US 2019/0127440 A1    May 2, 2019

(30) Foreign Application Priority Data
Apr. 5, 2016   (EP) .................... 16163883

(51) Int. Cl.
*C07K 14/715*  (2006.01)
*A61P 17/00*   (2006.01)
*A61P 37/08*   (2006.01)
*A61K 38/00*   (2006.01)

(52) U.S. Cl.
CPC .......... *C07K 14/7155* (2013.01); *A61P 17/00* (2018.01); *A61P 37/08* (2018.01); *C07K 14/715* (2013.01); *A61K 38/00* (2013.01); *C07K 2319/32* (2013.01)

(58) Field of Classification Search
None
See application file for complete search history.

(56) References Cited

U.S. PATENT DOCUMENTS

2014/0113370 A1 * 4/2014 Camphausen ......... C07K 14/78
435/328

FOREIGN PATENT DOCUMENTS

EP    2703414 A1   9/2008

OTHER PUBLICATIONS

Allakhverdi, et al. "Thymic Stromal Lymphopoietin Is Released by Human Epithelial Cells in Response to Microbes, Trauma, or Inflammation and Potently Activates Mast Cells." The Journal of Experimental Medicine. 204.2 (2007): 253-8.
PCT International Search Report and Written Opinion for Application No. PCT/EP2017/057944, dated Apr. 23, 2017.

* cited by examiner

*Primary Examiner* — James H Alstrum-Acevedo
*Assistant Examiner* — Tara L Martinez
(74) *Attorney, Agent, or Firm* — Patent Law Works, LLP

(57) ABSTRACT

The present invention relates to monomeric fusion proteins comprising the extracellular part of the thymic stromal lymphopoietin receptor (TSLPR) and the extracellular part of the interleukin-7 receptor alpha (IL-7Ralpha) as inhibitors of thymic stromal lymphopoietin (TSLP) activity. The invention relates further to the use of said inhibitors as a medicament in the treatment of—but not limited to—inflammatory diseases, cancer and fibrosis.

17 Claims, 7 Drawing Sheets
Specification includes a Sequence Listing.

(a) TSLP-trap1

(b) TSLP-trap2 a b (a)

$K_D = 3,2E\text{-}08$ M (b)

No interaction up to 100 nM of IL-7Ralpha (c)

$K_D = 1,2E\text{-}10$ M

A

B

C

ടടഞ1
TSLP INHIBITORS

FIELD OF THE INVENTION

The present invention relates to monomeric fusion proteins comprising the extracellular part of the thymic stromal lymphopoietin receptor (TSLPR) and the extracellular part of the interleukin-7 receptor alpha (IL-7Ralpha) as inhibitors of thymic stromal lymphopoietin (TSLP) activity. The invention relates further to the use of said inhibitors as a medicament in the treatment of—but not limited to—inflammatory diseases, cancer and fibrosis.

BACKGROUND

Thymic stromal lymphopoietin (TSLP) is an interleukin-2 (IL-2) family cytokine produced by epithelial cells at barrier surfaces in the lung and gut, and by epidermal keratinocytes in the skin. It regulates immunity by driving the activation of immature dendritic cells (DC), mast cells, basophils, eosinophils and lymphocytes into a type 2 polarizing phenotype (Bell et al., 2013; Ziegler, 2010, 2012; Ziegler and Artis, 2010; Ziegler et al., 2013). Cell signaling mediated by TSLP is initiated at the cell surface via a heteromeric receptor complex with its cognate receptor, TSLPR (encoded by CRLF2) (Pandey et al., 2000; Park et al., 2000), and IL-7Ralpha, a receptor that also serves as the cognate receptor for IL-7 to regulate T-cell development and homeostasis (Mackall et al., 2011). Indeed, the crystal structure of mouse TLSP in complex with TSLPR and IL-7Ralpha has revealed how TSLP establishes extensive interfaces with its two receptors to evoke membrane-proximal receptor-receptor contacts poised for intracellular signaling. In addition, binding of TSLP to TSLPR is a mechanistic prerequisite for recruitment of IL-7Ralpha to the high-affinity ternary complex (Verstraete et al., 2014).

Aberrant signaling by TSLP has serious consequences for human health and imprints a massive healthcare and socioeconomic footprint. This is because type 2 helper T cell (Th2)-mediated inflammatory responses primed by activated dendritic cells (DCs), are pivotal for the onset of widespread allergic diseases of the airways, skin and gut. In fact, TSLP is now widely considered to be the master regulator for most prevalent inflammatory allergic disorders, such as the triad of atopic diseases (asthma, atopic dermatitis and atopic rhinitis), chronic obstructive pulmonary disease (COPD), and eosinophilic esophagitis (Noti et al., 2013; Redhu and Gounni, 2012; Siracusa et al., 2013; Ziegler, 2012; Ziegler et al., 2013), and has been annotated as a genetic risk factor for the development of asthma (Hunninghake et al., 2010; Liu et al., 2012; Torgerson et al., 2011) and eosinophilic esophigitis (Rothenberg et al., 2010). In addition, there is a clear pathophysiological connection among some of these diseases. For instance, 70% of patients with atopic dermatitis go on to develop asthma via what has been called "atopic march" (Spergel, 2010), while adults with active asthma are strongly predisposed for acquiring COPD when compared to non-asthmatic individuals (Guerra, 2009). Several recent developments have added new dimensions to the pathophysiological pleiotropy of TSLP. First, TSLP mediated signaling has been identified as the molecular liaison between the skin epithelium and neuronal cells to trigger itch associated with atopic dermatitis (Wilson et al., 2013). Second, TSLP has been identified as a new molecular factor contributing to the development of psoriasis, a large-scale autoimmune disease, by virtue of its effects on IL-23 production by DC (Volpe et al., 2014). Third, TSLP has been reported to have causative effects in terms of tumor progression in breast- and pancreatic cancer (De Monte et al., 2011; Pedroza-Gonzalez et al., 2011), and genetic rearrangements and mutations in the TSLPR gene (CRLF2) have been reported in pediatric acute lymphoblastic leukemia (Perez-Andreu et al., 2013). Fourth, TSLP has been implicated in the pathogenesis of non-allergic diseases characterized by a type 2 immune response and in promoting organ fibrosis (Ying et al., 2015).

Considering the above described pathophysiological profile and the increasing prevalence of allergic diseases worldwide, it is no surprise that TSLP has emerged as therapeutic target, in particular for the treatment of atopic diseases (Borowski et al., 2013; Romeo et al., 2013, 2014; Zhang et al., 2011). In this regard, a recent study employing a primate animal model has shown that blockade of the TSLPR reduces allergic inflammation (Cheng et al., 2013). Recently, the validity of TSLP as a therapeutic target in humans was further demonstrated in a clinical trial in which asthmatic patients were treated with an anti-TSLP monoclonal antibody (Gauvreau et al., 2014). Nevertheless, despite proof of in vitro potency of the currently available agents that target the TSLP/TSLPR/IL-7Ralpha complex, the in vivo effects seem to be mild. Also uncertainties regarding the efficacy of monoclonal antibodies against TSLP may arise due to possible cross-reactivity with the recently described short form of human TSLP (Bjerkan et al., 2015; Fornasa et al., 2015). In addition, EP2703414 (Amgen Inc) discloses alternative TSLP blockers consisting of soluble huIL-7Ra-huTSLPR-Fc protein fusions which are dimeric and are very large fusion proteins. Intrinsic shortcomings of therapeutic monoclonal antibodies and the fusion proteins in EP2703414 are poor tissue penetration, Fc-mediated immunostimulatory effects, limitations in administration and dose indications and cost of production which necessitate the exploration of alternative strategies. Accordingly, and as there is no effective treatment available, there is an unmet need for a potent inhibitor of TSLP signaling that does not have the above mentioned limitations and which can be used for effective treatment of TSLP related diseases.

SUMMARY

It is surprisingly shown herein that a monomeric fusion protein comprising the extracellular part of the TSLPR and the extracellular part of the IL-7Ralpha (herein referred to as "TSLP-trap") can have strong TSLP neutralization activity. This is unexpected, as neither the extracellular TSLPR alone nor the extracellular IL-7Ralpha alone nor a mixture of both show a strong inhibitory activity on TSLP mediated signaling events.

It is an aspect of the present invention to provide monomeric fusion proteins comprising the extracellular part of the TSLPR and the extracellular part of the IL-7Ralpha.

In one embodiment, the invention envisages the monomeric fusion protein as described above, wherein said extracellular part of the TSLPR and said extracellular part of the IL-7Ralpha are connected by a linker, wherein said linker comprises at least 10 amino acids and/or wherein said linker is a GGS linker consisting of 5 to 20 GGS units (which corresponds with 15 to 60 amino acids).

In one embodiment, the invention envisages the monomeric fusion protein as described above, wherein said fusion protein comprises an amino acid sequence with at least 80% or at least 90% sequence identity with the amino acid sequence of SEQ ID No 1 and an amino acid sequence with at least 80% or at least 90% sequence identity with the amino acid sequence of SEQ ID No 2. Also envisaged is the fusion protein as described above, wherein said fusion protein comprises the amino acid sequence of SEQ ID No 1 and the amino acid sequence of SEQ ID No 2.

It is an aspect of the present invention to provide a nucleic acid encoding at least the fusion protein as described above.

It is an aspect of the present invention to provide a host cell comprising the nucleic acid as described above. Also envisaged is said host cell for use in the production of said fusion protein.

Also envisaged is the monomeric fusion protein as described above, for use as a medicament, for use in the treatment of an inflammatory disease (wherein said inflammatory disease is selected from the group consisting of asthma, chronic obstructive pulmonary disease, allergic rhinitis, atopic dermatitis, eosinophilic esophagitis, rheumatoid arthritis and psoriasis), and for the use in the treatment of cancer and fibrosis.

It is an aspect of the present invention to provide a pharmaceutical composition comprising the monomeric fusion protein as described above in association with a pharmaceutically acceptable carrier.

Objects of the present invention will be clear from the description that follows.

DETAILED DESCRIPTION

Figure 1:
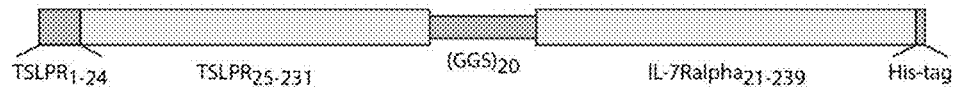
FIG. 1 shows a schematic representation of the monomeric TSLP-trap fusion proteins TSLP-trap1 (a) and TSLP-trap2 (b). (GGS)$_{20}$: linker consisting of twenty glycine-glycine-serine (GGS) repeats; pHLsec-SS: secretion signal of the pHLsec-vector (Aricescu et al., 2006); His-tag: polyhistidine tag. The ranges of amino acid residue numbers of the TSLPR and the IL-7Ralpha are indicated for both traps and relate to the human amino acid sequence.
Figure 1:
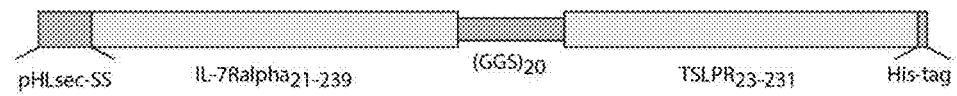

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 4th ed., Cold Spring Harbor Press, Plainsview, New York (2012); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

A "fusion protein" or chimeric protein is a protein created through joining of two or more proteins or protein parts that originally were separate proteins or parts of separate proteins.

A "monomeric fusion protein" is a monomeric chimeric protein created through joining of two or more proteins or protein parts that originally were separate proteins or parts of separate proteins. Hence, a monomeric fusion protein of the invention is different from a dimeric fusion protein described in EP2703414. Indeed, fusion proteins described in EP2703414 are Fc—fusion proteins which upon expression in a cell lead to dimers formed by sulfur (S-S) bridges between the Fc regions. As such the "monomeric fusion protein" of the invention is a single chain fusion protein which is different from a two chain fusion protein formed in EP2703414.

In the present invention with the wording "fusion protein" or "fusion protein of the invention" it is meant a "monomeric fusion protein".

"Protein", "polypeptide" or "peptide" refers to a polymer of amino acids and does not refer to a specific length of the molecule. This term also includes post-translational modifications, such as—but not limited to—glycosylation, phosphorylation and acetylation.

The term "extracellular part" (or ectodomain) of a protein, as used herein, refers to the portion of an integral membrane protein that is exposed to the extracellular space, wherein said integral membrane protein contains one or more transmembrane domain/s made up predominantly of hydrophobic amino acids. Such an extracellular part mainly comprises hydrophilic amino acids, which are typically positioned at the surface of a folded structure of a protein, and thus is soluble in an aqueous environment. For most cell surface receptor proteins, extracellular parts or extracellular domains serve to bind specific ligands, while intracellular domains play an important role in signal transduction.

A "linker", as used herein, is any linker or spacer that connects two or more proteins or two or more protein parts. This definition includes peptide-based linkers as well as non-peptide linkers.

The term "nucleic acid", as used herein, refers to a polymeric form of nucleotides of any length, either deoxyribonucleotides or ribonucleotides, or analogs thereof. Nucleic acids may have any three-dimensional structure, and may perform any function, known or unknown. Non-limiting examples of nucleic acids include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

"Treatment" and "treating," as used herein refer to both therapeutic treatment and prophylactic or preventative measures, wherein the objective is to inhibit or slow down (lessen) the targeted disorder (e.g. cancer) or symptom of the disorder, or to improve a symptom, even if the treatment is partial or ultimately unsuccessful. Those in need of treatment include those already diagnosed with the disorder as well as those prone or predisposed to contract the disorder or those in whom the disorder is to be prevented. For example, in tumor (e.g. cancer) treatment, a therapeutic agent can directly decrease the pathology of tumor cells, or render the tumor cells more susceptible to treatment by other therapeutic agents or by the subject's own immune system.

As used herein, "cancer" refers to any uncontrolled growth of cells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject. For example, cancers can include benign and malignant cancers, polyps, hyperplasia, as well as dormant tumors or micrometastases.

A first aspect of the present invention relates to a monomeric fusion protein that comprises the extracellular part (ectodomain) of the TSLPR and the extracellular part (ectodomain) of the IL-7Ralpha. In yet another embodiment the invention provides a monomeric fusion protein that comprises the functional extracellular part (functional ectodomain) of the TSLPR and the functional extracellular part (functional ectodomain) of the IL-7Ralpha. The TSLPR and the IL-7Ralpha are known to the person skilled in the art (Uniprot ID: Q9HC73 for human TSLPR, Uniprot ID: P16871 for human IL-7Ralpha). Functional assays to measure the binding of TSLP with the TSLPR or to measure the binding of the IL-7Ralpha to IL7 or to TSLP are known to the person skilled in the art. It is known that the N-terminal and carboxy-terminal ends of extracellular receptors tolerate some flexibility in order to maintain their functionality. Based on rational design we calculated that SEQ ID NO: 1 (corresponding with TSLPR) and SEQ ID NO: 2 (corresponding with IL-7Ralpha) are functional extracellular parts of TSLPR and IL-7Ralpha. In another embodiment, the functional TSLPR ectodomain is derived from a mammal and the functional IL-7Ralpha ectodomain is derived from a mammal. Mammal refers to any member of the class Mammalia, including, without limitations, humans and nonhuman primates such as chimpanzees and other apes and monkey species; farm animals such as cattle, sheep, pigs, goats, lamas and horses; domestic mammals such as dogs and cats; laboratory animals including rodents such as mice, rats, and guinea pigs, and the like. The term does not denote a particular age or sex. Thus, adult and newborn subjects, as well as fetuses, whether male or female, are intended to be included within the scope of this term. In one specific embodiment, the TSLPR extracellular part is derived from the human TSLPR and the IL-7Ralpha extracellular part is derived from the human IL-7Ralpha. Alternatively, homologues of those proteins may be used. Homologues encompass proteins having amino acid substitutions (such as mutations), deletions and/or insertions relative to the unmodified protein in question and having similar biological and functional activity as the unmodified protein from which they are derived. In various embodiments, the fusion protein comprises an amino acid sequence that is at least 80% or at least 90% identical to SEQ ID No 1 and an amino acid sequence that is at least 80% or at least 90% identical to SEQ ID No 2. For example, the fusion protein may comprise a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID No 1 and a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID No 2. In a specific embodiment, the fusion protein comprises the sequence of SEQ ID No 1 and the sequence of SEQ ID No 2. The fusion protein of the present application may be expressed with a secretion signal, such as—but not limited to—the secretion signal of the human TSLPR (SEQ ID No 5) or the secretion signal of the pHLsec-vector (SEQ ID No 6). Typically, said secretion signals are cleaved during the process of protein maturation and are not present in the mature, secreted protein. The fusion of the above described fusion protein may be at the amino-terminal or at the carboxy-terminal end of the extracellular part of the TSLPR. This allows flexibility of the combination of the described extracellular parts. In one embodiment, the fusion is at the amino-terminal end of the extracellular part of the TSLPR. In one embodiment, the fusion is at the carboxy-terminal end of the extracellular part of the TSLPR. In one specific embodiment, the fusion protein is the human TSLP-trap1 of SEQ ID No 3. In one specific embodiment, the fusion protein is the human TSLP-trap2 of SEQ ID No 4.

According to particular embodiments, the extracellular part of the TSLPR and the extracellular part of the IL-7Ralpha are connected by a linker. In one embodiment, there is no particular limitation on the length or the flexibility of the linker used in the fusion protein of the invention. In one embodiment, the linker may be a peptide-based linker, such as a suitable amino acid sequence. In particular, the linker may be an amino acid sequence of 1 to 60, 1 to 50, 1 to 40, 1 to 30, 1 to 20, 1 to 10 or 1 to 5 amino acid residues. In one embodiment, said linker comprises at least 10 amino acids, at least 15 amino acids, at least 20 amino acids, at least 25 amino acids or at least 30 amino acids. In one embodiment, said linker is a glycine-glycine-serine (GGS) linker, i.e. said linker consists of GGS units. In a specific embodiment, said GGS linker consists of 5 to 20 GGS units (which corresponds with 15 to 60 amino acids). In one embodiment, the linker is a non-peptide linker. In one particular embodiment, said non-peptide linker is not based on polyethylene glycol (PEG). In one particular embodiment, said non-peptide linker is a PEG based spacer. In one particular embodiment, said PEG linker is activated with sulfhydryl-reactive chemical groups, such as—but not limited to—haloacetyls, maleimides, aziridines, acryloyls, arylating agents, vinylsulfones, pyridyl disulfides, TNB-thiols, BMH (bismaleimidohexane), BMB (1,4-bismaleimidobutane), bismaleimidoethane, dithiobismaleimidoethane, tris(2-maleimidoethyl) amine and disulfide reducing agents. In one particular embodiment, said PEG linker is activated with chemical groups reactive to amino- and/or carboxyl-groups in proteins, such as—but not limited to—N-hydroxysuccinimide, primary amine groups and tert-butyloxycarbonyl protected-amino groups. In one particular embodiment, said PEG linker is activated with sulfhydryl-reactive chemical groups and chemical groups reactive to amino- and/or carboxyl-groups in proteins. Also envisaged are homobifunctional cross-linkers allowing linkage of the same type of functional group. Also envisaged are heterobifunctional cross-linkers allowing linkage of two distinct functional groups. In one embodiment, the linker can be conjugated to the extracellular part of the TSLPR and to the extracellular part of the IL-7Ralpha via—but not limited to—naturally occurring cysteine residues in the sequences of the TSLPR and/or the IL-7Ralpha or via engineered cysteines.

The monomeric fusion protein as described herein may contain a protein tag, such as—but not limited to—a histidine (His) tag. In a different embodiment, the monomeric fusion protein as described herein contains no protein tag.

Said monomeric fusion protein may be any construct comprising two or more proteins or protein parts comprising the TSLPR ectodomain and the IL-7Ralpha ectodomain. That is to say, said monomeric fusion protein may comprise further moieties. Said further moieties may bind to TSLP or not. As a non-limiting example, said monomeric fusion protein may be linked (chemically or otherwise) to one or more groups or moieties that extend the half-life (such as—but not limited to—PEG), so as to provide a derivative of a fusion protein of the invention with increased half-life.

In various embodiments, the binding affinity of the monomeric fusion protein of the invention for the full-length and/or mature forms and/or isoforms and/or splice variants and/or fragments and/or monomeric and/or multimeric forms and/or any other naturally occurring or synthetic analogs, variants, or mutants (including monomeric and/or multimeric forms) of TSLP may be described by the equilibrium dissociation constant ($K_D$). In various embodiments, the monomeric fusion protein binds to the full-length and/or mature forms and/or isoforms and/or splice variants and/or fragments and/or any other naturally occurring or synthetic analogs, variants, or mutants (including monomeric and/or multimeric forms) of TSLP with a $K_D$ of less than 100 nM, 90 nM, 80 nM, 70 nM, 60 nM, 50 nM, 40 nM, 30 nM, 20 nM, 10 nM, 5 nM, 2.5 nM, 1 nM, 900 pM, 800 pM, 700 pM, 600 pM, 500 pM, 400 pM, 300 pM, 200 pM, 100 pM, 90 pM, 80 pM, 70 pM, 60 pM, 50 pM, 40 pM, 30 pM, 20 pM or 10 pM.

In some embodiments, the monomeric fusion protein described herein includes derivatives that are modified, i.e. by the covalent attachment of any type of molecule to the fusion protein such that covalent attachment does not prevent the activity of the protein. For example, but not by way of limitation, derivatives include fusion proteins that have been modified by, inter alia, glycosylation, lipidation, acetylation, pegylation, phosphorylation, amidation, derivatization by known protecting/blocking groups, proteolytic cleavage, linkage to a ligand or other protein etc. Any of numerous chemical modifications can be carried out by techniques known to the skilled person.

"Inhibition", as used herein, refers to the fact that the monomeric fusion protein interferes with/inhibits/prevents/ reverses or slows the ability of TSLP to induce signaling events as measured in an in vitro potency assay, such as—but not limited to—a TSLP induced STAT5 reporter assay. Inhibition, also referred to as neutralization, can mean full neutralization (no TSLP induced signal is observable) or may mean partial neutralization. The neutralization activity typically will be evaluated against a suitable control (e.g. treatment with an irrelevant protein), as will be readily chosen by the skilled person. For fusion proteins with known concentration, the inhibitory activity can be expressed as 50% inhibitory concentration (IC50). The IC50 is the fusion protein concentration at which 50% inhibition (or neutralization) is achieved. It is a measure of the inhibitory potential, also referred to as potency, of a protein. In various embodiments, the fusion protein as described herein inhibits TSLP induced signaling with a potency of less than 100 nM, 90 nM, 80 nM, 70 nM, 60 nM, 50 nM, 40 nM, 30 nM, 20 nM, 10 nM, 5 nM, 2.5 nM, 1 nM, 900 pM, 800 pM, 700 pM, 600 pM, 500 pM, 400 pM, 300 pM, 200 pM, 100 pM, 90 pM, 80 pM, 70 pM, 60 pM, 50 pM, 40 pM, 30 pM, 20 pM or 10 pM.

According to a further aspect, the fusion proteins are not provided as such, but are provided as nucleic acid, i.e. nucleic acid molecules encoding fusion proteins as herein described. According to a further aspect, also provided are recombinant expression vectors comprising such nucleic acids or nucleic acid molecules. In another aspect, a host cell comprising the above described nucleic acid or vector is envisaged. A host cell, as used herein, may be any cell that is suitable for production of said fusion protein. Typically, the nucleic acids will have been introduced in the host cell by transfection, transformation or transduction techniques, although the way in which the nucleic acid is introduced in the host cell is not limiting the invention. The host cells comprising the nucleic acids (or vectors) described herein are particularly suited for production of the fusion proteins. Thus, such use for production is explicitly envisaged herein. Illustrative host cells are *E.coli* cells, Chinese hamster ovary (CHO) cells, human embryonic kidney 293 (HEK 293) cells, HeLa cells, monkey kidney cells (COS) and yeast cells. Transformed host cells can be grown under conditions that permit the host cells to express the genes that encode the fusion protein of the invention. Specific expression and purification conditions will vary depending upon the expression system employed. For example, if a gene is to be expressed in *E. coli*, it is first cloned into an expression vector by positioning the engineered gene downstream from a suitable bacterial promoter, e.g. Trp or Tac, and a prokaryotic signal sequence. In another example, if the engineered gene is to be expressed in eukaryotic host cells, e.g. CHO cells, it is first inserted into an expression vector containing for example, a suitable eukaryotic promoter, a secretion signal, enhancers, and various introns. The gene construct can be introduced into the host cells using transfection, transformation, or transduction techniques. The fusion protein of the invention can be produced by growing a host cell transfected with an expression vector encoding the fusion protein under conditions that permit expression of the protein. Following expression, the protein can be harvested and purified using techniques well known in the art, e.g. affinity tags such as glutathione-S-transferase (GST) and histidine (His) tags or by chromatography. In an embodiment, the fusion protein comprises a His-tag.

According to an embodiment, the monomeric fusion proteins are provided herein for use in medicine. That is to say, the fusion proteins are provided for use as a medicament. The same goes for the nucleic acid molecules or recombinant expression vectors encoding the fusion proteins, i.e. it is envisaged that nucleic acid molecules or vectors encoding the fusion proteins are provided for use as a medicament. According to particular embodiments, the fusion proteins (or nucleic acids or vectors encoding them) are provided for use in the treatment of inflammatory diseases or conditions, such as inflammation, acute inflammation, chronic inflammation, respiratory disease, atherosclerosis, restenosis, asthma, allergic rhinitis, atopic dermatitis, psoriasis, chronic obstructive pulmonary disease (COPD), eosinophilic esophagitis, septic shock, rheumatoid arthritis, inflammatory bowel disease, inflammatory pelvic disease, pain, ocular inflammatory disease, celiac disease, Leigh Syndrome, glycerol kinase deficiency, familial eosinophilia (FE), autosomal recessive spastic ataxia, laryngeal inflammatory disease, tuberculosis, chronic cholecystitis, bronchiectasis, silicosis and other pneumoconioses. In a specific embodiment, the fusion proteins described herein are provided for use in the treatment of asthma, COPD, allergic rhinitis, atopic dermatitis, eosinophilic esophagitis, rheumatoid arthritis and psoriasis.

According to particular embodiments, the monomeric fusion proteins (or nucleic acids or vectors encoding them) are provided for use in the treatment of cancer. Illustrative cancers that may be treated include, but are not limited to, basal cell carcinoma, biliary tract cancer, bladder cancer, bone cancer, brain and central nervous system cancer, breast cancer, cancer of the peritoneum, cervical cancer, choriocarcinoma, colon and rectum cancer, connective tissue cancer, cancer of the digestive system, endometrial cancer, esophageal cancer, eye cancer, cancer of the head and neck, gastric cancer (including gastrointestinal cancer), glioblastoma, hepatic carcinoma, hepatoma, intra-epithelial neoplasm, kidney or renal cancer, larynx cancer, leukemia, liver cancer, lung cancer (e.g. small-cell lung cancer, non-small cell lung cancer, adenocarcinoma of the lung, and squamous carcinoma of the lung), melanoma, myeloma, neuroblastoma, oral cavity cancer (lip, tongue, mouth, and pharynx), ovarian cancer, pancreatic cancer, prostate cancer, retinoblastoma, rhabdomyosarcoma, rectal cancer, cancer of the respiratory system, salivary gland carcinoma, sarcoma, skin cancer, squamous cell cancer, stomach cancer, testicular cancer, thyroid cancer, uterine or endometrial cancer, cancer of the urinary system, vulval cancer, lymphoma including Hodgkin's and non-Hodgkin's lymphoma, as well as B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's Macroglobulinemia, chronic lymphocytic leukemia (CLL), acute lymphoblastic leukemia (ALL), Hairy cell leukemia, chronic myeloblastic leukemia, as well as other carcinomas and sarcomas, and post-transplant lymphoproliferative disorder (PTLD), as well as abnormal vascular proliferation associated with phakomatoses, edema (e.g. associated with brain tumors), and Meigs' syndrome.

According to particular embodiments, the monomeric fusion proteins (or nucleic acids or vectors encoding them) are provided for use in the treatment of fibrosis. Illustrative examples include, but are not limited to organ fibrosis, pulmonary fibrosis, airway remodeling, myofibroblast hyperplasia, asthmatic airway remodeling and fibrosis, idiopathic pulmonary fibrosis and cutaneous systematic sclerosis.

This is equivalent as saying that methods are provided for the treatment of inflammatory diseases, cancer or fibrosis for a subject in need thereof, comprising administering a therapeutically effective amount of the fusion protein to said subject. Such methods typically will result in improvement of symptoms of the disease in said subject. Here also, the monomeric fusion protein may be provided as a protein, as a pharmaceutical composition or may be administered as a nucleic acid molecule encoding the monomeric fusion protein or as a vector comprising such nucleic acid molecule. If the monomeric fusion protein is administered as a protein, different routes of administration can be envisaged. For example—but not by way of limitation—routes of administration include: oral, intradermal, intramuscular, intraperitoneal, intravenous, subcutaneous, intranasal, epidural, sublingual, intranasal, intracerebral, intravaginal, transdermal, rectally, by inhalation, or topically. Administration can be local or systemic. The mode of administration can be left to the discretion of the practitioner, and depends in-part upon the site of the medical condition. In most instances, administration results in the release of the fusion protein described herein into the bloodstream. In case the fusion protein is provided as a nucleic acid or vector, it is particularly envisaged that the monomeric fusion protein is administered through gene therapy.

In a further aspect, the disclosure contemplates a pharmaceutical composition comprising the monomeric fusion protein as described above, in association with a pharmaceutically acceptable carrier. Typically, such pharmaceutical compositions comprise at least the fusion protein. Said pharmaceutical compositions may comprise further moieties. Said further moieties may bind to TSLP or not. Pharmaceutically acceptable carriers are known to the person skilled in the art, and are inherently non-toxic and nontherapeutic. Carriers may be, as a non-limiting example, Ringer's solution, dextrose solution or Hank's solution. Non aqueous solutions such as fixed oils and ethyl oleate may also be used. A preferred carrier is 5% dextrose in saline. The pharmaceutically acceptable carrier may contain minor amounts of additives such as substances that enhance isotonicity and chemical stability, including buffers and preservatives. It is envisaged herein that the pharmaceutical compositions are provided for use as a medicament. Particularly, they are provided for use in the treatment of inflammatory diseases, cancer or fibrosis. This is equivalent as stating that methods are provided for the treatment of inflammatory diseases, cancer or fibrosis for a subject in need thereof, comprising administering a pharmaceutical composition as described herein to said subject. Here also, different routes of administration of the pharmaceutical composition can be envisaged. For example—but not by way of limitation—routes of administration include: oral, intradermal, intramuscular, intraperitoneal, intravenous, subcutaneous, intranasal, epidural, sublingual, intranasal, intracerebral, intravaginal, transdermal, rectally, by inhalation, or topically. Administration can be local or systemic. The mode of administration can be left to the discretion of the practitioner, and depends in-part upon the site of the medical condition. In most instances, administration results in the release of the pharmaceutical composition described herein into the bloodstream. In various embodiments, the pharmaceutical composition of the present invention is co-administered in conjunction with additional therapeutic agent(s). Co-administration can be simultaneous or sequential.

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Materials and Methods to the Examples

Design of the TSLP-traps

Human TSLP-trap1 consists of the human TSLPR ectodomain (residues 25 to 231 from Uniprot ID: Q9HC73, SEQ ID No 7) interconnected to the human IL-7Ralpha ectodomain (residues 21 to 239 from Uniprot ID: P16871, SEQ ID No 8) through a $(GGS)_{20}$-linker region that connects the C-terminus of the TSLPR ectodomain and the N-terminus of the IL-7Ralpha ectodomain.

Human TSLP-trap2 consists of the human IL-7Ralpha ectodomain (Uniprot ID: P16871, residues 21 to 239) interconnected to the human TSLPR ectodomain (Uniprot ID: Q9HC73, residues 23 to 231) through a $(GGS)_{20}$-linker region that connects the C-terminus of the IL-7Ralpha ectodomain and the N-terminus of the TSLPR ectodomain.

To enable secretion of TSLP-traps from mammalian cells a secretion signal is included in the open reading frame encoding the TSLP-trap proteins. This secretion signal is proteolytically removed from the mature protein. For TSLP-trap1, the native secretion signal of human TSLPR is used (residues 1 to 24 from Uniprot ID: Q9HC73; SEQ ID No 5), while for TSLP-trap2 the signal peptide from the pHLsec-vector is used (Aricescu et al., 2006; SEQ ID No 6). Both TSLP-trap1 and TSLP-trap2 carry a His-tag at their C-terminus. The human TSLP-trap1 and TSLP-trap2 fusion proteins are shown schematically in FIG. 1.

Cloning and Recombinant Production of TSLP, TSLPR, IL-7Ralpha and TSLP-Traps cDNA fragments encoding full-length human TSLP_R127A_R130S (NP_149024.1; residue 1-159), the extracellular fragments of human TSLPR (NP_071431.2; residue 1 -221) and human IL-7Ralpha (NP_002176.2; residue 1-239) and human TSLP-trap1 were cloned into the multicloning site of the pcDNA4/TO-expression vector (Thermofisher) in frame with a C-terminal His-tag. Human TSLP carries the R127A and R130S mutations (TSLP_R127A_R130S) to remove a potential furin cleavage site (Lyman et al., 2013). Human TSLP-trap2 was cloned into a modified version of the pcDNA4/TO vector which carried the signal peptide from the pHLsec-vector (SEQ ID No 6) at its multicloning site.

Stable, tetracycline-inducible cell lines for TSLP_R127A_R130S and the TSLPR and IL-7Ralpha ecotodomains were generated in HEK293S MGAT1−/− cells (Reeves et al., 2002). Stable, tetracycline-inducible cell lines for TSLP-trap1 and TSLP-trap2 were generated in T-REx™-293 cells (Thermo Fisher Scientific). HEK293S MGAT1−/− and T-REx™-293 cells were grown in high-glucose DMEM medium supplemented with 10% fetal calf serum, 106 units.L-1 penicillin G and 1 gL-1 streptomycin in a 5% $CO_2$ atmosphere at 37° C. For the growth of T-REx™-293 cells, the medium was supplemented with 5 μg/mL blasticidin.

Figure 2:
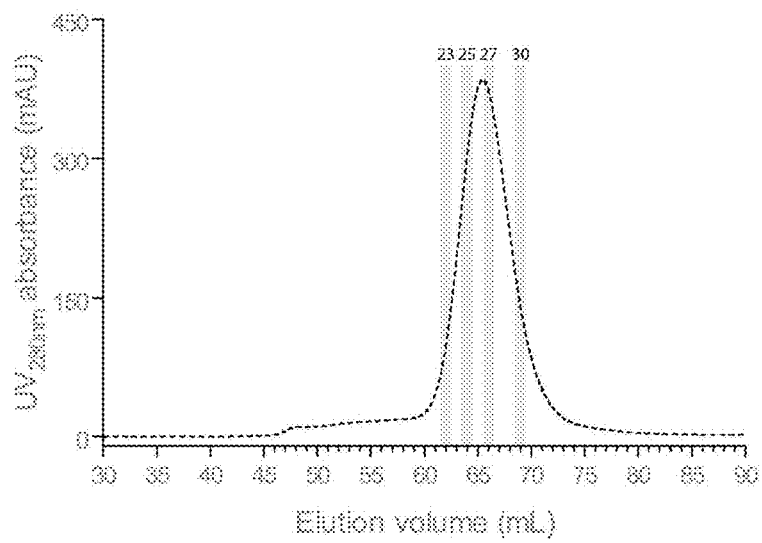
FIG. 2 shows the analysis of purified human TSLP-trap1 protein. (a) Size exclusion chromatography (SEC) elution profile of purified TSLP-trap1 on a Superdex 200 column. (b) SDS-PAGE gel of purified TSLP-trap1 under reducing conditions. Protein bands were visualized using the TGX stain-free technology (Biorad). The peak fractions analyzed on the SDS-PAGE gel are indicated on the SEC profile in (a). Following mixing with Laemmli-buffer, samples were either submitted to denaturation (boiled) or not (non-boiled) before loading.
Figure 2:
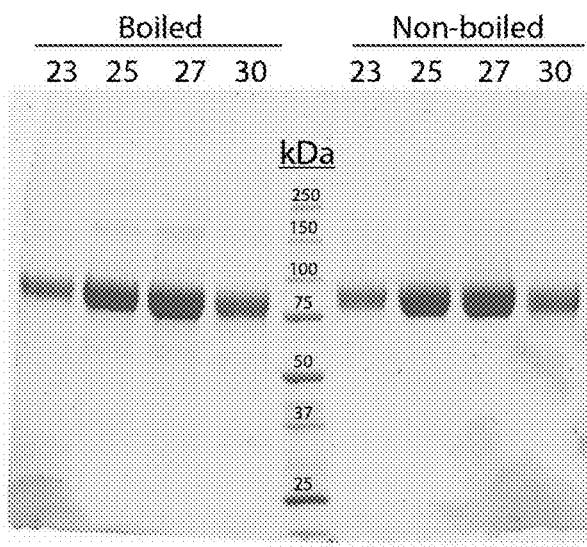

Stable cell lines were generated by selection with 200 μg/mL zeocine as described in Verstraete et al., 2011. To induce expression, the medium of confluently grown cells was replaced with serum-free medium supplemented with 2 μg/mL tetracycline. Recombinant protein expression from pools of stable transfected cells was confirmed by Western blot analysis using an HRP-coupled antibody directed against the C-terminal His-tag (Invitrogen, catalogue No. R931-25) or small-scale immobilized metal affinity chromatography (IMAC) purifications in batch mode using 2 mL of conditioned medium (using Ni Sepharose beads from GE Healthcare). For large-scale expression experiments, pools of stable transfected cells were expanded to thirty 175 cm2 tissue-culture flasks. Four to five days following induction with tetracycline the conditioned medium was harvested and cleared by centrifugation and filtration through a 0.22 μm bottle top filter. Recombinant proteins were captured from the cleared conditioned medium by IMAC purification using a cOmplete His-Tag purification column (Roche) and further purified by size-exclusion chromatography (SEC) using a Superdex 200 or Superdex 75 column (GE Healthcare) with HBS pH 7.4 as running buffer. As an example, the SEC elution profile for TSLP-trap1 and an SDS-PAGE gel (under reducing conditions) demonstrate the sample homogeneity and purity of the TSLP-trap1 preparation (FIG. 2).

Production of a Neutralizing Anti-TSLP Antibody

A neutralizing human anti-TSLP IgG2 monoclonal antibody (Mab) with a lambda light chain, and its derived Fab-fragment were recombinantly produced by transient transfection in HEK293T cells. cDNA fragments encoding the light chain and heavy chain for antibody A5 described in patent WO2009035577 were ordered from Gen9. To generate a Fab fragment, the $V_H$-$C_H1$ heavy fragment was generated by PCR. All cDNAs were cloned between the AgeI and KpnI sites of the pHLsec expression plasmid, in frame with the signal peptide of the vector (Aricescu et al. 2006). The heavy chain and the $V_H$-$C_H1$ heavy chain fragment were cloned in frame with the C-terminal hexahistidine tag, while the light chain carried a stop codon. The full-length Mab or Fab-fragment were produced by co-transfecting HEK293T cells with expression plasmids for the light chain and heavy chain or $V_H$-$C_H1$-fragment in a 1:1 ratio. The Mab or Fab-fragment were purified from the conditioned medium by IMAC and SEC.

Biolayer Interferometry

The binding affinity and binding kinetics for the interaction between TSLP_R127A_R130S and the TSLPR ectodomain, the IL-7Ralpha ectodomain and TSLP-trap1 were investigated by biolayer interferometry (BLI). Streptavidin-coated biosensors were functionalized with biotinylated TSLP_R127A_R130S and quenched with a 10 μg/ml biotin solution and then exposed to different concentrations of ligand.

To produce biotinylated TSLP, a cDNA fragment encoding TSLP_R127A_R130S was cloned between the EcoRl and KpnI sites of the pHL-AVITAG vector (Aricescu et al., 2006). Prior the transfection in HEK293T cells, the culture medium was changed to serum-free DMEM medium to which 100 μM D-biotin was added. To allow specific C-terminal in vivo biotinylation the pHL-TSLP_R127A_R130S-AVITAG construct was co-transfected with the pDisplay-BirA-ER plasmid (Howarth et al., 2008) in a 5:1 ratio. Five days post-transfection conditioned medium was harvested and loaded onto a Ni sepharose column (GE Healthcare). Recombinant proteins were eluted with imidazole and loaded onto a Superdex 75 column with HBS as running buffer.

All BLI experiments were performed in PBS buffer supplemented with 0.01% (w/v) BSA and 0.002% (v/v) Tween 20, with an Octet RED96 instrument (ForteBio), operating at 25° C.

To verify that no aspecific binding was present during the interaction assay, non-functionalized biosensors were used as a control. All data were fitted with the ForteBio Data Analysis 9.0.0.4 software using a 1:1 ligand model. The reported values for the fitted parameters represent the average (and standard deviation) from three replicate measurements.

Constructs for the TSLP Induced STAT5 Reporter Assay pMET7-Flag-hTSLPR and pMET7-HA-hIL-7Ralpha allow the expression of a full-length FLAG-tagged human TSLPR and full-length HA-tagged human IL-7Ralpha. pMET7-Flag-hTSLPR was created by ligating a codon optimized hTSLPR cDNA sequence into the ClaI/XbaI opened pMet7-FLAG-mTSLP vector (Verstraete et al., 2014). pMET7-HA-hIL-7Ralpha was created by ligating a codon optimized hIL-7Ralpha cDNA sequence into the BspEI/XbaI opened pMet7-HA-mIL-7Ralpha vector (Verstraete et al., 2014).

TSLP Induced STAT5 Reporter Assay

For measuring TSLP signaling in HEK293T cells, HEK293T cells were co-transfected with 1.5 ng pMET7-Flag-hTSLPR, 1.5 ng pMET7-HA-hIL-7Ralpha, 893 ng empty pMET7 vector and 23.5 ng pGL3-β-casein-luci reporter plasmid per well of a 6-well plate. For transfection, we incubated the DNA with linear PEI 25 kda (Polysciences) at a 2.17:1 PEI:DNA ratio for 12 minutes in serum-free Optimem I medium (Life technologies), before addition of this DNA:PEI mix to the cells. The pGL3-β-caseinduci luciferase reporter contains 5 repeated STAT5-responsive motifs of the β-casein promoter (Verstraete et al., 2014). The day after transfection, the cells were detached with cell dissociation buffer (Life Technologies), and resuspended in DMEM+10% foetal bovine serum. 3% of the cells were seeded in 50 μl medium per well in 96 well plates and stimulated 50 μl medium with increasing concentrations of mammalian-cell derived recombinant TSLP (TSLP_R127A_R130S). On day two after transfection, the luciferase activity in the 96 well plates was determined on an Envision chemiluminescence counter as described previously (Peelman et al., 2004). Fold induction of luciferase activity was calculated by dividing the luminescence signal (cps) of the TSLP stimulated cells by the luminescence signal of the unstimulated cells. The data were fitted to a log agonist versus response curve in GraphPad Prism.

Inhibition in the TSLP Induced STAT5 Reporter Assay

To study the effect of different inhibitors (traps, receptor ectodomains, anti-TSLP antibody or derived Fab fragment) on TSLP induced STAT5 reporter assays, HEK293T cells were seeded and transfected as described above. The day after transfection, the cells were detached with cell dissociation buffer (Life Technologies), and resuspended in DMEM+10% foetal bovine serum. 3% of the cells were seeded in 50 μl medium per well in 96 well plates. In a separate plate, mammalian cell derived recombinant TSLP (TSLP_R127A_R130S) in medium was incubated with increasing concentrations of the inhibitors for 30 minutes at room temperature. After this pre-incubation, 50 μl of this TSLP-inhibitor mix was added to the seeded cells. The reported concentrations for inhibitor and TSLP (10 pM) are their final concentrations in this 100 μl volume. Cells were incubated overnight with this mixture and STAT5 reporter luciferase activity was measured 24 hours after the start of the stimulation, as described above. Fold induction of luciferase activity was calculated by dividing the luminescence signal (cps) of the TSLP stimulated cells by the luminescence signal of the unstimulated cells. The data were fitted to a log inhibitor versus response curve in GraphPad Prism.

Mouse Strains

C57Bl/6J (WT) mice were purchased at Janvier labs and TSLPR$^{-/-}$ (Crlf2$^{-/-}$) mice were provided by M. Comeau. Mice were maintained in the animal facility of the VIB-UGent Center of Inflammation Research under specific pathogen-free conditions. Experiments were approved by the animal ethical committees of the Ghent University and the VIB-UGent Center for Inflammation Research.

Example 1

Generation of the TSLP-Traps

The engineered human TSLP-traps encode monomeric fusion proteins consisting of the extracellular regions of human TSLPR and human IL-7Ralpha, separated by an amino acid linker, here exemplified by a flexible Gly-Gly-Ser (GGS) linker. In one example of a human TSLP-trap, the GGS-linker region connects the C-terminus of the TSLPR ectodomain to the N-terminus of the IL-7Ralpha ectodomain, (denoted as TSLP-trap1, FIG. 1a). In another example, the GGS-linker region connects the C-terminus of the IL-7Ralpha ectodomain to the N-terminus of the TSLPR ectodomain (denoted as TSLP-trap2, FIG. 1b). TSLP-traps contain a signal peptide leading to the secretion of the recombinant protein into the medium fraction when expressed in mammalian cells. As a signal peptide, either the native secretion signal of TSLPR or IL-7Ralpha can be used, as for example in TSLP-trap1 which carries the native secretion signal of TSLPR. Alternatively, TSLP-trap fusion proteins may carry another secretion signal, as for example in TSLP-trap2 which carries the secretion signal of the pHLsec-vector (Aricescu et al., 2006). The C-terminal His-tag allows easy detection and purification of TLSP-traps from conditioned medium of transfected cells. TSLP-trap1 and TSLP-trap2 were purified by a combination of IMAC and SEC to a purity of ~95%, judged by SDS-PAGE analysis. As an example, the final SEC-profile and SDS-PAGE analysis for purified TSLP-trap1 are shown in FIG. 2.

Example 2

The TSLP-Trap has High Affinity for TSLP

Figure 3:
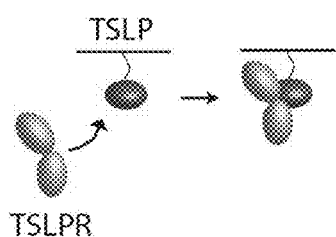
FIG. 3 shows the affinities to TSLP, evaluated by biolayer interferometry. The interferometric wavelength shift (nm) in function of time is plotted as a grey solid line. Fitted curves are plotted as black dashed lines. The concentrations on the plots refer to the concentrations of the ligand analyzed: (a) TSLPR, (b) IL-7Ralpha and (c) TSLP-trap1. The reported $K_D$-value represents the average from three replicate measurements.
Figure 3:
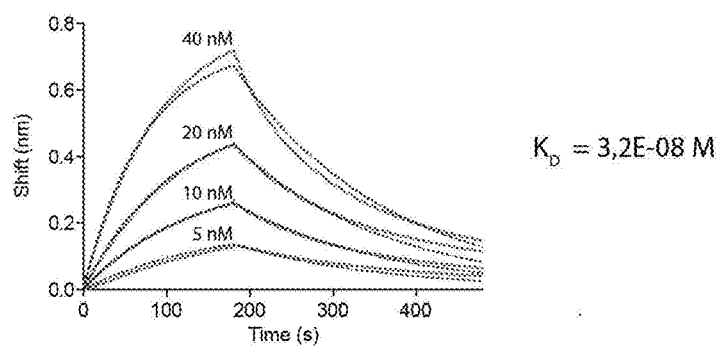
Figure 3:
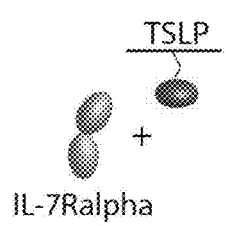
Figure 3:
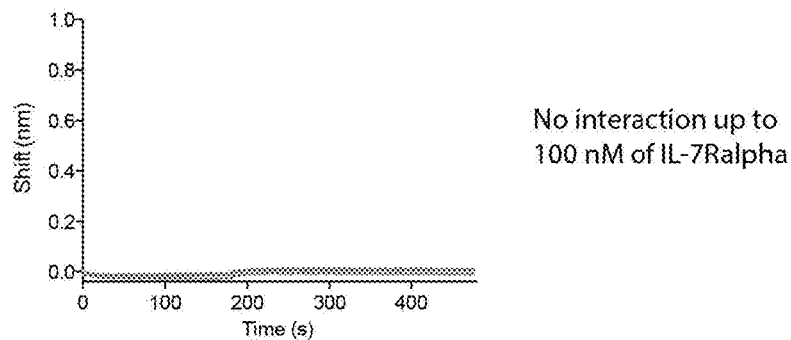
Figure 3:
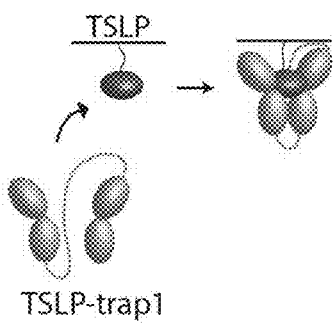
Figure 3:
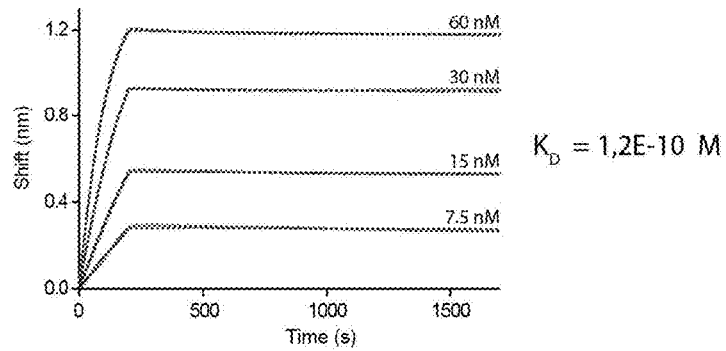

To characterize the interaction between TSLP and the TSLPR ectodomain, the IL-7Ralpha ectodomain and TSLP-trap1 real time kinetic bio-layer interferometry (BLI) experiments were performed. As ligand C-terminally biotinylated human TSLP was immobilized on streptavidin-coated biosensor tips. Firstly, it was determined that the TSLPR ectodomain binds to TSLP with an affinity ($K_D$) of 3,2E-08 M and an association rate ($k_{on}$) of 1,7E+05 $M^{-1}s^{-1}$ and a dissociation rate ($k_{off}$) of 5,2E-03 $s^{-1}$ (FIG. 3a), while for IL-7Ralpha no interaction was observed up to a concentration of 100 nM (FIG. 3b). Using higher concentrations of IL-7Ralpha to probe the possible low affinity interaction between TSLP and IL-7Ralpha resulted in non-specific binding of IL-7Ralpha under the experimental conditions used.

Surprisingly, it is shown herein that TSLP-trap1 binds very strongly to immobilized TSLP with an affinity ($K_D$) of 1,2E-10 M and an association rate ($k_{on}$) of 1,4E+05 M-1s-1 and a dissociation rate ($k_{off}$) of 1,7E-05 s-1 (FIG. 3c). The kinetic profile of the TSLP-trap reveals that this strong binding affinity arises from a markedly lower dissociation rate constant ($k_{off}$=1,72E-05 $s^{-1}$) as compared with the dissociation rate of the unfused ectodomains.

Example 3

The TSLP-Trap is a Potent Inhibitor of TSLP

Figure 4:
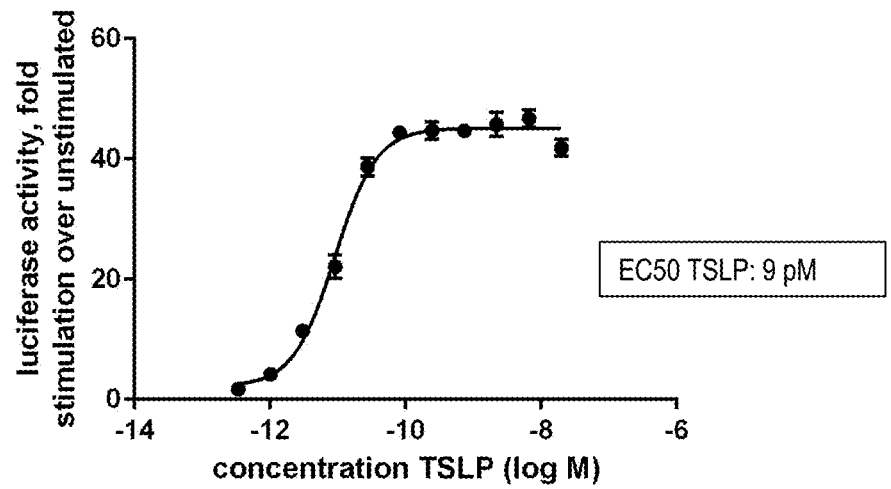
FIG. 4 shows the dose response curve of TSLP binding to HEK293T cells transfected with pMET7-Flag-hTSLPR, pMET7-HA-hIL-7Ralpha and pGL3-β-caseinduci, as evaluated in the STAT5-luciferase reporter assay. Cells were stimulated with increasing concentrations of TSLP and the effect on luciferase activity was determined. TSLP has an EC50 value of 9 pM in this assay.
Figure 5:
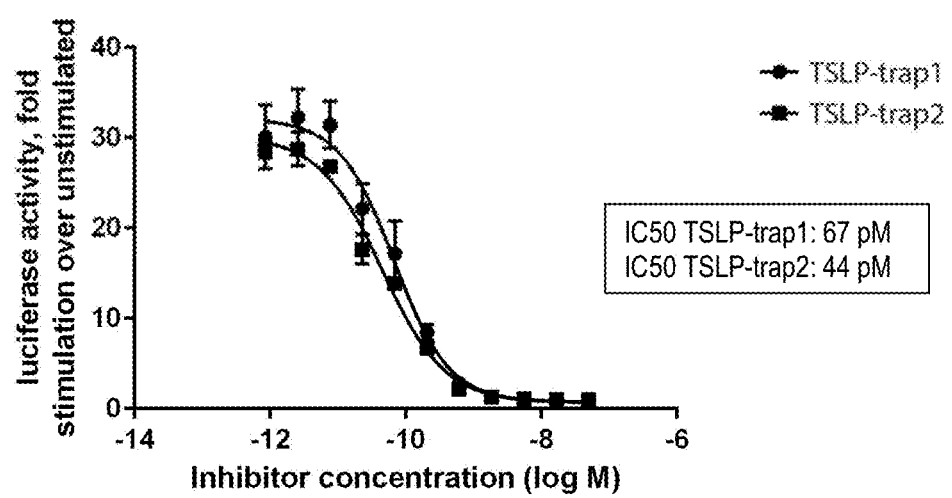
FIG. 5 shows the inhibitory effect of the TSLP-traps on the TSLP induced STAT5-luciferase reporter assay in HEK293T cells. Cells were co-incubated with increasing concentrations of either TSLP-trap1 or TSLP-trap2 and 10 pM TSLP. In this assay, the TSLP-trap1 has an IC50 value of 67 pM and the TSLP-trap2 has an IC50 value of 44 pM.
Figure 6:
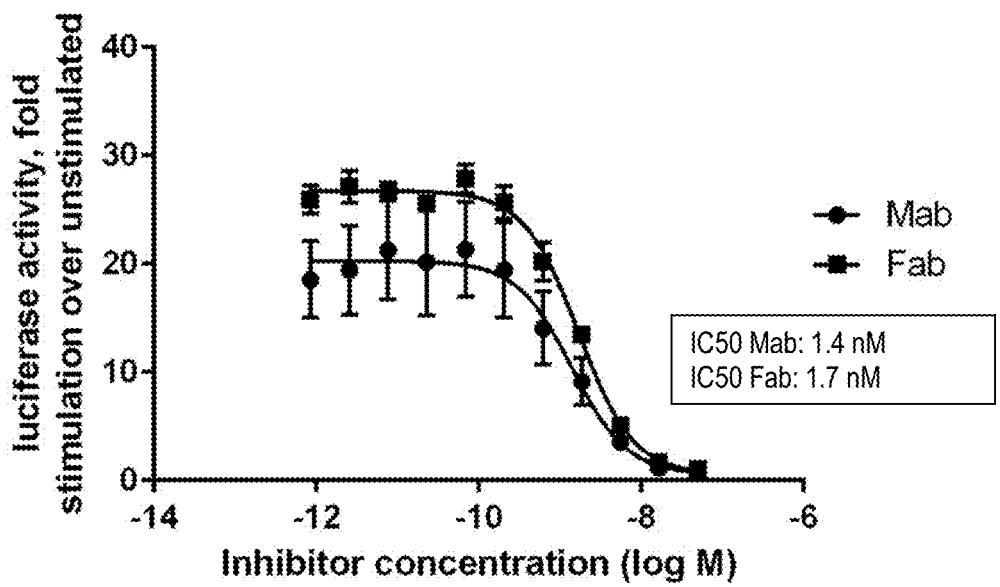
FIG. 6 shows the inhibitory effect of an anti-TSLP monoclonal antibody (Mab, described in WO2009035577) and its derived Fab fragment on the TSLP induced STAT5-luciferase reporter assay in HEK293T cells. Cells were co-incubated with increasing concentrations of either Mab or Fab fragment and 10 pM TSLP. In this assay, the antibody has an IC50 of 1.4 nM and the Fab fragment has an IC50 value of 1.7 nM.
Figure 7:
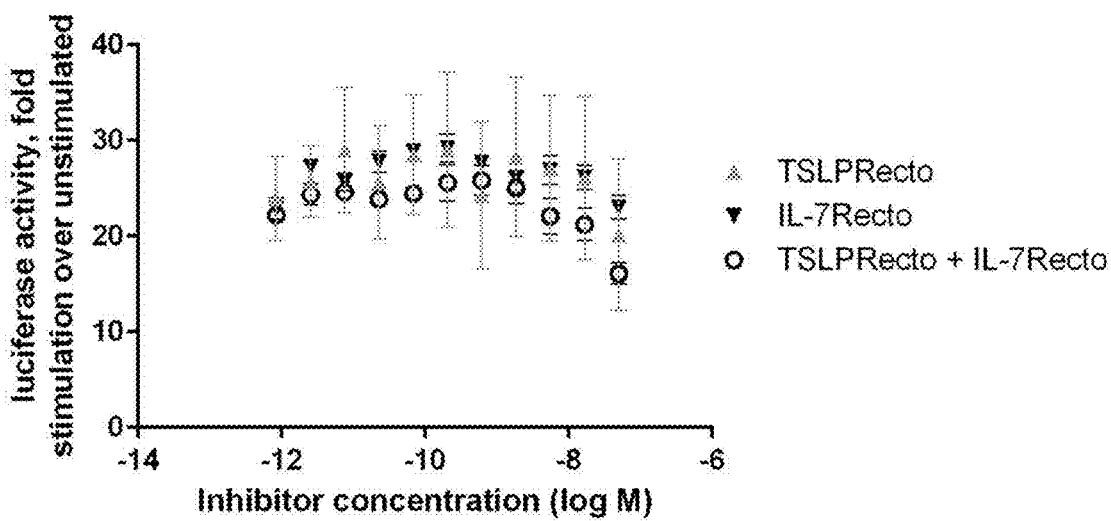
FIG. 7 shows the effect of the TSLPR extracellular part (TSLPRecto) and/or the IL-7Ralpha extracellular part (IL-7Recto) on the TSLP induced STAT5-luciferase reporter assay in HEK293T cells. Cells were co-incubated with 10 pM TSLP combined with different concentrations of the extracellular part of the TSLPR or of the IL-7Ralpha or with the extracellular parts of both receptors (as separate protein chains, not fused together via a linker). The extracellular parts show slight inhibition only at the highest tested concentration in this assay.

The potential of the engineered TSLP-traps to block cytokine activity of TSLP was evaluated by an in vitro bioassay. The inhibitory potency of the TSLP-traps was compared to the TSLPR and the IL-7Ralpha ectodomain alone, to a combination of both ectodomains, and to a neutralizing anti-TSLP monoclonal antibody (Mab, described in WO2009035577) and its derived Fab fragment. Their ability to block was evaluated in a TSLP induced STAT5 reporter assay in HEK293T cells transfected with full-length TSLPR and IL-7Ralpha. Stimulation of transfected cells with TSLP strongly induces STAT5-dependent luciferase activity with an EC50 value of 9 pM (FIG. 4.). Pre-incubation of a fixed concentration of TSLP (10 pM) with increasing concentrations of either TSLP-trap1 or TSLP-trap2 effectively inhibits TSLP dependent STAT5-activation, with IC50 values of 67 pM and 44 pM for TSLP-trap1 and TSLP-trap2, respectively (FIG. 5). Pre-incubation of 10 pM TSLP with a neutralizing human anti-TSLP IgG2 monoclonal antibody (Mab) described in patent WO2009035577, or its derived Fab-fragment resulted in IC50 values of 1.4 nM and 1.7 nM, respectively (FIG. 6). On the other hand, pre-incubation of 10 pM TSLP with the TSLPR or the IL-7Ralpha ectodomain alone, or with a combination of both ectodomains did not result in significant inhibition (FIG. 6.). This surprisingly demonstrates that linking the TSLPR and IL-7Ralpha ectodomains creates an enormeous advantage when aiming to inhibit TSLP signaling. Moreover, the here described TSLP-traps show a 20- to 40-fold lower IC50 value as compared to a neutralizing anti-TSLP antibody, indicating the inhibitory potency of the TSLP-traps.

Example 4

Figure 8:
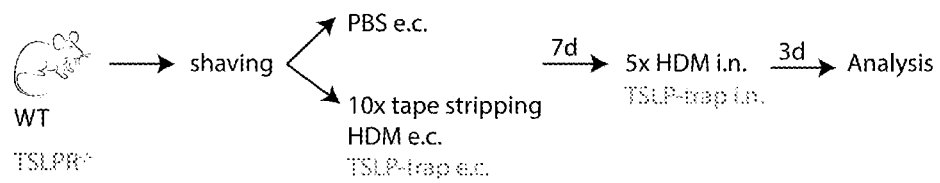
FIG. 8 A) WT mice or TSLPR$^{-/-}$ mice were shaved and epicutaneously (e.c.) exposed to PBS (negative control) or 10× tape stripped and subsequently e.c. sensitized to house dust mite (HDM). Seven days later, all mice received daily HDM challenge in the lungs during 5 consecutive days and analysis was performed 3 days after the last challenge. One group was treated with TSLP-trap; 50 µg subcutaneously during e.c. sensitization and 25 µg intranasally (i.n.) during each HDM challenge. B) Cell infiltrations in bronchoalveolar lavage fluid (BALF) and C) cytokine secretion by mediastinal lymph node (MLN) cells, restimulated with HDM for 3 days ex vivo. Data represent means±SEM, n=3-5 (p<0,05 calculated by Mann-Whitney U test; * compared to PBS group, # compared to other).
Figure 8:
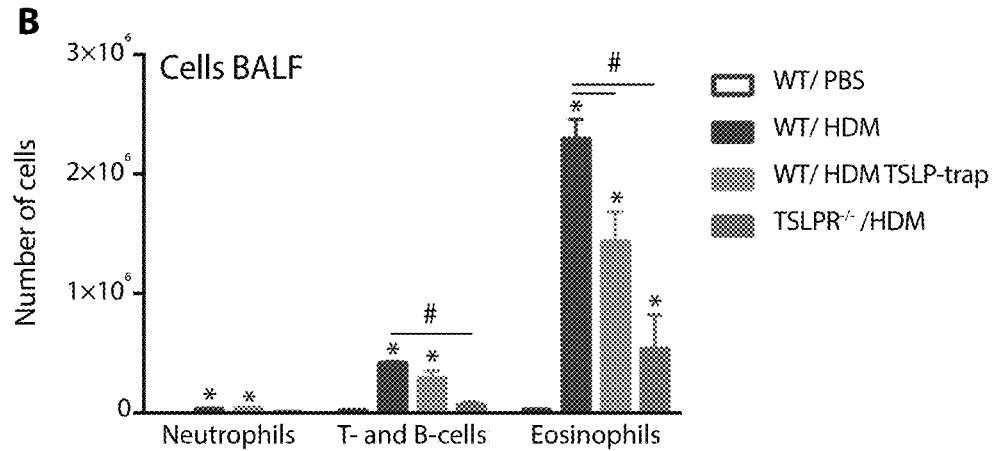
Figure 8:
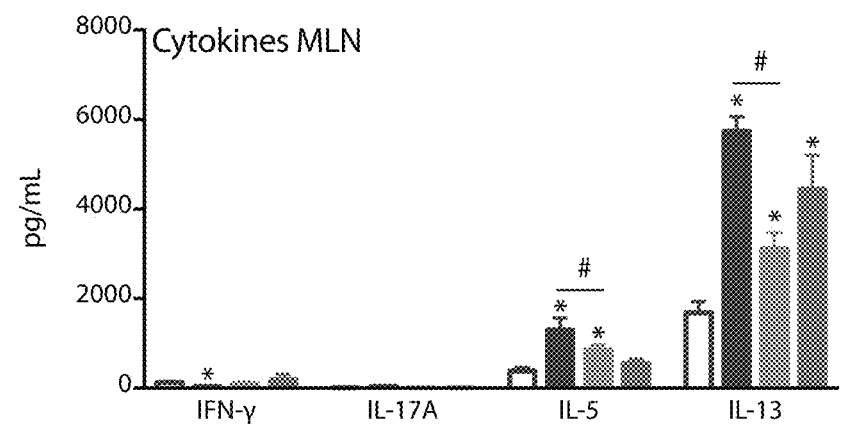

Effect of TSLP-Trap in a Mouse Model of HDM-Induced Allergic Airway Inflammation WT and TSLPR$^{-/-}$ mice were shaved on the skin of the back, 10× tape-stripped and exposed to 10 µg HDM under an occlusive patch on the skin. As a negative control, WT mice were exposed to PBS under a patch on shaved skin. One group (TSLP-trap) received an injection of 50 µg TSLP-trap subcutaneously (s.c.) at the time of HDM exposure and this treatment was repeated 8 hours later. Seven days later, all mice were challenged with HDM via the lungs during 5 consecutive days and the TSLP-trap group was simultaneously treated with intranasal administration (i.n.) of 25 µg TSLP-trap (see FIG. 8A). Features of allergic airway inflammation were assessed 3 days after the last challenge.

The lack of Th2 response in TSLPR-deficient mice indicates that TSLP signaling contributed to the development of lung eosinophilia in a model of allergic airway inflammation, induced via epicutaneous (e.c.) sensitization to HDM. Therapeutic removal of TSLP by injection of TSLP-trap was also able to significantly reduce the infiltration of eosinophils in the BALF (see FIG. 8B). Production of Th2 cytokines (IL-5 and IL-13) by Mediastinal Lymph Node (MLN) cells, which were restimulated with HDM during 3 days ex vivo, was significantly reduced when mice were previously treated with TSLP-trap. These experiments indicate that inactivation of TSLP signaling by TSLP-trap results in a reduction of Th2-mediated allergic airway inflammation in a model of e.c. HDM sensitization (see FIG. 8C). We conclude that the TSLP-Trap is able to suppress lung eosinophilia in a mouse model of HDM-induced allergic airway inflammation.

Example 5

Effect of TSLP-Trap in an Atopic Dermatitis Mouse Model

Figure 9:
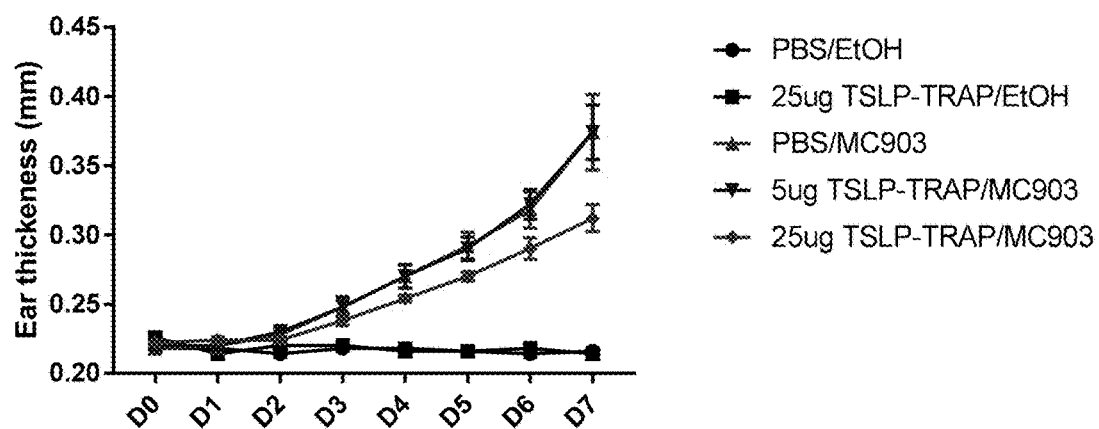
FIG. 9 Mice were treated every day for 7 days with PBS or TSLP-TRAP (5 µg or 25 µg), followed by topical application of MC903 (1nmol) or ethanol on the ear. Ear thickness was measured daily using a dial thickness gauge. Data are represented as±SEM (n=5)
Figure 10:
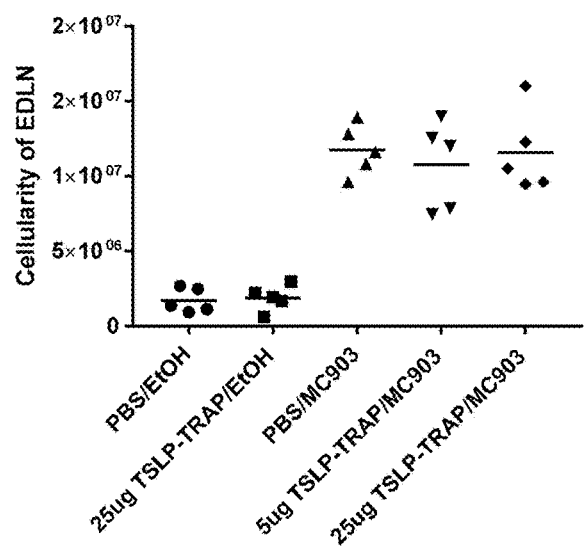
FIG. 10 Determination of the cellularity of the ear draining lymph node (EDLN) under the different conditions FIG. 11 Lymphocytes of the ear draining lymph node were isolated and counted. 180.000 lymphocytes were restimulated in vitro with CD3/CD28. After 72 hours of stimulation, the medium was collected and assayed for IL-13 production by ELISA. Data are represented as±SEM (n=5).
Figure 11:
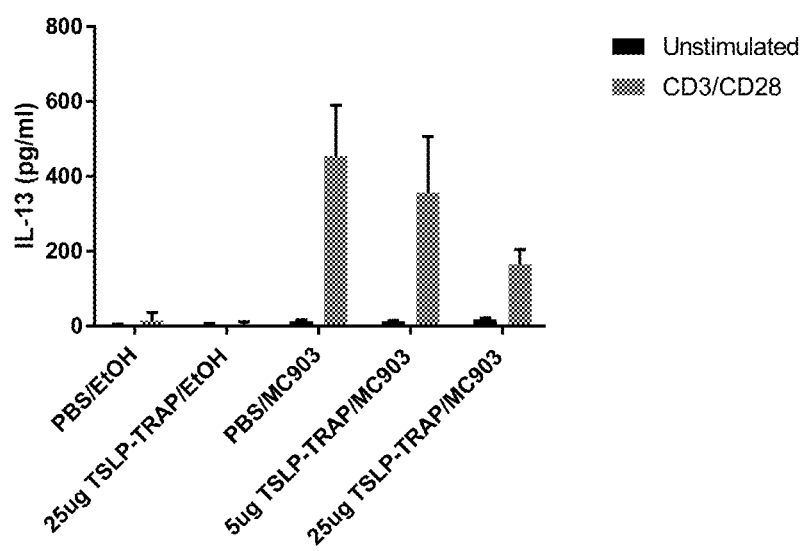

To study the potential of the TSLP-trap as a therapeutic against atopic dermatitis, we tested the ability of the TSLP-trap to inhibit atopic dermatitis induced by the vitamin D3 analogue MC903. In this mouse model, atopic dermatitis is induced by MC903 in a TSLP-dependent manner (Li M. et al (2009) *J. Invest. Dermatol.* 129: 498-502; Li M. et al. (2006) *Proc. Natl. Acad. Sci USA* 103: 11736-41). During 7 days, mice were injected intraperitoneally every day with TSLP-trap (5 µg or 25 µg) or PBS followed by topical application of MC903 (1 nmol) or ethanol onto the ear. To assess atopic dermatitis-like inflammation, the thickening of the ear was measured daily using a dial thickness gauge. Mice treated with a dose of 25 µg TSLP-trap showed less thickening of the ears upon MC903 application compared to PBS-treated controls (FIG. 9). After 7 days, mice were sacrificed and lymphocytes from the ear draining lymph node (EDLN) were isolated. The cellularity of the EDLN was increased upon MC903 treatment but did not differ between the groups treated with PBS and 5 µg and 25 µg TSLP-trap (FIG. 10). Next, IL-13 cytokine production by the lymphocytes was assayed in response to in vitro CD3/CD28 re-stimulation. Lymphocytes derived from mice treated with MC903 showed strong induction of IL-13 cytokine production which was less pronounced in mice that received 25 µg TSLP-trap (FIG. 11). Together these data point to a protective role for TSLP-trap in a mouse model for atopic dermatitis.

| Sequences |
| --- |
| SEQ ID No 1: amino acid sequence of part of the extracellular region of the human TSLPR (residues 29- 211)<br>GVQIQIIYFNLETVQVTWNASKYSRTNLTFHYRFNGDEAYDQCTNYLLQE<br>GHTSGCLLDAEQRDDILYFSIRNGTHPVFTASRWMVYYLKPSSPKHVRFS<br>WHQDAVTVTCSDLSYGDLLYEVQYRSPFDTEWQSKQENTCNVTIEGLDAE<br>KCYSFWVRVKAMEDVYGPDTYPSDWSEVTCWQR |
| SEQ ID No 2: amino acid sequence of part of the extracellular region of the human IL-7Ralpha (residues 38 -229)<br>YSFSCYSQLEVNGSQHSLTCAFEDPDVNTTNLEFEICGALVEVKCLNFRK<br>LQEIYFIETKKFLLIGKSNICVKVGEKSLTCKKIDLTTIVKPEAPFDLSV<br>IYREGANDFVVTFNTSHLQKKYVKVLMHDVAYRQEKDENKWTHVNLSSTK<br>LTLLQRKLQPAAMYEIKVRSIPDHYFKGFWSEWSPSYYFRTP |
| SEQ ID No 3: human TSLP-trap1 amino acid sequence (without secretion signal)<br>GAAEGVQIQIIYFNLETVQVTWNASKYSRTNLTFHYRFNGDEAYDQCTNY<br>LLQEGHTSGCLLDAEQRDDILYFSIRNGTHPVFTASRWMVYYLKPSSPKH<br>VRFSWHQDAVTVTCSDLSYGDLLYEVQYRSPFDTEWQSKQENTCNVTIEG<br>LDAEKCYSFWVRVKAMEDVYGPDTYPSDWSEVTCWQRGEIRDACAETPTP<br>PKPKLSKSRGGSGGSGGSGGSGGSGGSGGSGGSGGSGGSGGSGGSGGSGG<br>SGGSGGSGGSGGSGGSGGSLQESGYAQNGDLEDAELDDYSFSCYSQLEVN<br>GSQHSLTCAFEDPDVNTTNLEFEICGALVEVKCLNFRKLQEIYFIETKKF<br>LLIGKSNICVKVGEKSLTCKKIDLTTIVKPEAPFDLSVIYREGANDFVVT<br>FNTSHLQKKYVKVLMHDVAYRQEKDENKWTHVNLSSTKLTLLQRKLQPAA<br>MYEIKVRSIPDHYFKGFWSEWSPSYYFRTPEINNSSGEMDGTKHHHHHH |
| SEQ ID No 4: human TSLP-trap2 amino acid sequence (without secretion signal)<br>ETGESGYAQNGDLEDAELDDYSFSCYSQLEVNGSQHSLTCAFEDPDVNTT<br>NLEFEICGALVEVKCLNFRKLQEIYFIETKKFLLIGKSNICVKVGEKSLT<br>CKKIDLTTIVKPEAPFDLSVIYREGANDFVVTFNTSHLQKKYVKVLMHDV<br>AYRQEKDENKWTHVNLSSTKLTLLQRKLQPAAMYEIKVRSIPDHYFKGFW<br>SEWSPSYYFRTPEINNSSGEMDSRGGSGGSGGSGGSGGSGGSGGSGGSGG<br>SGGSGGSGGSGGSGGSGGSGGSGGSGGSGGSLQGGGAAEGVQIQIIY<br>FNLETVQVTWNASKYSRTNLTFHYRFNGDEAYDQCTNYLLQEGHTSGCLL |
| DAEQRDDILYFSIRNGTHPVFTASRWMVYYLKPSSPKHVRFSWHQDAVTV<br>TCSDLSYGDLLYEVQYRSPFDTEWQSKQENTCNVTIEGLDAEKCYSFWVR<br>VKAMEDVYGPDTYPSDWSEVTCWQRGEIRDACAETPTPPKPKLSKGTKHH<br>HHHH |
| SEQ ID No 5: secretion signal of human TSLPR<br>MGRLVLLWGAAVFLLGGWMALGQG |
| SEQ ID No 6: secretion signal of the pHLsec-vector (Aricescu et al., 2006)<br>MGILPSPGMPALLSLVSLLSVLLMGCVA |
| SEQ ID No 7: amino acid sequence of the extracellular part of human TSLPR (residues 25-231) as depicted in FIG. 1<br>GAAEGVQIQIIYFNLETVQVTWNASKYSRTNLTFHYRFNGDEAYDQCTNY<br>LLQEGHTSGCLLDAEQRDDILYFSIRNGTHPVFTASRWMVYYLKPSSPKH<br>VRFSWHQDAVTVTCSDLSYGDLLYEVQYRSPFDTEWQSKQENTCNVTIEG<br>LDAEKCYSFWVRVKAMEDVYGPDTYPSDWSEVTCWQRGEIRDACAETPTP<br>PKPKLSK |
| SEQ ID No 8: amino acid sequence of the extracellular part of human IL-7Ralpha (residues 21-239) as depicted in FIG. 1<br>ESGYAQNGDLEDAELDDYSFSCYSQLEVNGSQHSLTCAFEDPDVNTTNLE<br>FEICGALVEVKCLNFRKLQEIYFIETKKFLLIGKSNICVKVGEKSLTCKK<br>IDLTTIVKPEAPFDLSVIYREGANDFVVTFNTSHLQKKYVKVLMHDVAYR<br>QEKDENKWTHVNLSSTKLTLLQRKLQPAAMYEIKVRSIPDHYFKGFWSEW<br>SPSYYFRTPEINNSSGEMD |

REFERENCES

Aricescu, A. R., Lu, W., and Jones, E. Y. (2006). A time- and cost-efficient system for high-level protein production in mammalian cells. Acta Crystallogr D Biol Crystallogr 62, 1243-1250.

Bell, B. D., Kitajima, M., Larson, R. P., Stoklasek, T. A., Dang, K., Sakamoto, K., Wagner, K. U., Reizis, B., Hennighausen, L., and Ziegler, S. F. (2013). The transcription factor STAT5 is critical in dendritic cells for the development of TH2 but not TH1 responses. Nat Immunol 14, 364-371.

Bjerkan, L., Schreurs, O., Engen, S. A., Jahnsen, F. L., Baekkevold, E. S., Blix, I. J., and Schenck, K. (2015). The short form of TSLP is constitutively translated in human keratinocytes and has characteristics of an antimicrobial peptide. Mucosal immunology 8, 49-56.

Borowski, A., Vetter, T., Kuepper, M., Wohlmann, A., Krause, S., Lorenzen, T., Virchow, J. C., Luttmann, W., and Friedrich, K. (2013). Expression analysis and specific blockade of the receptor for human thymic stromal lymphopoietin (TSLP) by novel antibodies to the human TSLPRalpha receptor chain. Cytokine 61, 546-555.

Cheng, D. T., Ma, C., Niewoehner, J., Dahl, M., Tsai, A., Zhang, J., Gonsiorek, W., Apparsundaram, S., Pashine, A., Ravindran, P., et al. (2013). Thymic stromal lymphopoietin receptor blockade reduces allergic inflammation in a cynomolgus monkey model of asthma. J Allergy Clin Immunol 132, 455-462.

De Monte, L., Reni, M., Tassi, E., Clavenna, D., Papa, I., Recalde, H., Braga, M., Di Carlo, V., Doglioni, C., and Protti, M. P. (2011). Intratumor T helper type 2 cell infiltrate correlates with cancer-associated fibroblast thymic stromal lymphopoietin production and reduced survival in pancreatic cancer. J Exp Med 208, 469-478.

Fornasa, G., Tsilingiri, K., Caprioli, F., Botti, F., Mapelli, M., Meller, S., Kislat, A., Homey, B., Di Sabatino, A., Sonzogni, A., et al. (2015). Dichotomy of short and long thymic stromal lymphopoietin isoforms in inflammatory disorders of the bowel and skin. J Allergy Clin Immunol 136, 413-422.

Gauvreau, G. M., O'Byrne, P. M., Boulet, L. P., Wang, Y., Cockcroft, D., Bigler, J., FitzGerald, J. M., Boedigheimer, M., Davis, B. E., Dias, C., et al. (2014). Effects of an anti-TSLP antibody on allergen-induced asthmatic responses. The New England journal of medicine 370, 2102-2110.

Guerra, S. (2009). Asthma and chronic obstructive pulmonary disease. Current opinion in allergy and clinical immunology 9, 409-416.

Hunninghake, G. M., Soto-Quiros, M. E., Avila, L., Kim, H. P., Lasky-Su, J., Rafaels, N., Ruczinski, I., Beaty, T. H., Mathias, R. A., Barnes, K. C., et al. (2010). TSLP polymorphisms are associated with asthma in a sex-specific fashion. Allergy 65, 1566-1575.

Howarth, M., & Ting, A. Y. (2008). Imaging proteins in live mammalian cells with biotin ligase and monovalent streptavidin. Nature protocols, 3, 534-545.Liu, W., Xu, L. S., Liu, Q. J., Dong, F. Z., Qiu, R. F., Wen, M. C., Han, Y. L., Tang, N. B., Kang, L. J., Wu, J. X., et al. (2012). Two single nucleotide polymorphisms in TSLP gene are associated with asthma susceptibility in Chinese Han population. Experimental lung research 38, 375-382.

Lyman, S. D., Van Ness K. P. and Paxton R. J. (2013). Modified human thymic stromal lymphopoietin. Patent US20130023647.

Mackall, C. L., Fry, T. J., and Gress, R. E. (2011). Harnessing the biology of IL-7 for therapeutic application. Nat Rev Immunol 11, 330-342.

Noti, M., Wojno, E. D., Kim, B. S., Siracusa, M. C., Giacomin, P. R., Nair, M. G., Benitez, A. J., Ruymann, K. R., Muir, A. B., Hill, D. A., et al. (2013). Thymic stromal lymphopoietin-elicited basophil responses promote eosinophilic esophagitis. Nature medicine 19, 1005-1013.

Pandey, A., Ozaki, K., Baumann, H., Levin, S. D., Puel, A., Farr, A. G., Ziegler, S. F., Leonard, W. J., and Lodish, H. F. (2000). Cloning of a receptor subunit required for signaling by thymic stromal lymphopoietin. Nat Immunol 1, 59-64.

Park, L. S., Martin, U., Garka, K., Gliniak, B., Di Santo, J. P., Muller, W., Largaespada, D. A., Copeland, N. G., Jenkins, N. A., Farr, A. G., et al. (2000). Cloning of the murine thymic stromal lymphopoietin (TSLP) receptor: Formation of a functional heteromeric complex requires interleukin 7 receptor. J Exp Med 192, 659-670.

Pedroza-Gonzalez, A., Xu, K., Wu, T. C., Aspord, C., Tindle, S., Marches, F., Gallegos, M., Burton, E. C., Savino, D., Hori, T., et al. (2011). Thymic stromal lymphopoietin fosters human breast tumor growth by promoting type 2 inflammation. J Exp Med 208, 479-490.

Peelman, F. et al. (2004). Mapping of the leptin binding sites and design of a leptin antagonist. Journal of Biological Chemistry, 279, 41038-41046.Perez-Andreu, V., Roberts, K. G., Harvey, R. C., Yang, W., Cheng, C., Pei, D., Xu, H., Gastier-Foster, J., E, S., Lim, J. Y., et al. (2013). Inherited GATA3 variants are associated with Ph-like childhood acute lymphoblastic leukemia and risk of relapse. Nature genetics 45, 1494-1498.

Redhu, N. S., and Gounni, A. S. (2012). Function and mechanisms of TSLP/TSLPR complex in asthma and COPD. Clinical and experimental allergy : journal of the British Society for Allergy and Clinical Immunology 42, 994-1005.Reeves, P. J., Callewaert, N., Contreras, R., & Khorana, H. G. (2002). Structure and function in rhodopsin: high-level expression of rhodopsin with restricted and homogeneous N-glycosylation by a tetracycline-inducible N-acetylglucosaminyltransferase I-negative HEK293S stable mammalian cell line. Proceedings of the National Academy of Sciences, 99, 13419-13424.

Romeo, M. J., Agrawal, R., Pomes, A., and Woodfolk, J. A. (2013). A molecular perspective on T2-promoting cytokine receptors in patients with allergic disease. J Allergy Clin Immunol.

Romeo, M. J., Agrawal, R., Pomes, A., and Woodfolk, J. A. (2014). A molecular perspective on TH2-promoting cytokine receptors in patients with allergic disease. J Allergy Clin Immunol 133, 952-960.

Rothenberg, M. E., Spergel, J. M., Sherrill, J. D., Annaiah, K., Martin, L. J., Cianferoni, A., Gober, L., Kim, C., Glessner, J., Frackelton, E., et al. (2010). Common variants at 5q22 associate with pediatric eosinophilic esophagitis. Nature genetics 42, 289-291.

Siracusa, M. C., Saenz, S. A., Tait Wojno, E. D., Kim, B. S., Osborne, L. C., Ziegler, C. G., Benitez, A. J., Ruymann, K. R., Farber, D. L., Sleiman, P. M., et al. (2013). Thymic stromal lymphopoietin-mediated extramedullary hematopoiesis promotes allergic inflammation. Immunity 39, 1158-1170.

Spergel, J. M. (2010). From atopic dermatitis to asthma: the atopic march. Annals of allergy, asthma & immunology : official publication of the American College of Allergy, Asthma, & Immunology 105, 99-106; quiz 107-109, 117.

Torgerson, D. G., Ampleford, E. J., Chiu, G. Y., Gauderman, W. J., Gignoux, C. R., Graves, P. E., Himes, B. E., Levin, A. M., Mathias, R. A., Hancock, D. B., et al. (2011). Meta-analysis of genome-wide association studies of asthma in ethnically diverse North American populations. Nature genetics 43, 887-892.

Verstraete, K. et al. (2011). Inducible production of recombinant human Flt3 ectodomain variants in mammalian cells and preliminary crystallographic analysis of Flt3 ligand-receptor complexes. Acta Crystallographica Section F: Structural Biology and Crystallization Communications, 325-331.Verstraete, K., van Schie, L., Vyncke, L., Bloch, Y., Tavernier, J., Pauwels, E., Peelman, F., and Savvides, S. N. (2014). Structural basis of the proinflammatory signaling complex mediated by TSLP. Nature structural & molecular biology 21, 375-382.

Volpe, E., Pattarini, L., Martinez-Cingolani, C., Meller, S., Donnadieu, M. H., Bogiatzi, S. I., Fernandez, M. I., Touzot, M., Bichet, J. C., Reyal, F., et al. (2014). Thymic stromal lymphopoietin links keratinocytes and dendritic cell-derived IL-23 in patients with psoriasis. J Allergy Clin Immunol 134, 373-381.

Wilson, S. R., The, L., Batia, L. M., Beattie, K., Katibah, G. E., McClain, S. P., Pellegrino, M., Estandian, D. M., and Bautista, D. M. (2013). The Epithelial Cell-Derived Atopic Dermatitis Cytokine TSLP Activates Neurons to Induce Itch. Cell 155, 285-295.

Ying, G., Zhang, Y., Tang, G., and Chen, S. (2015). Functions of thymic stromal lymphopoietin in non-allergic diseases. Cellular immunology 295, 144-149.

Zhang, F., Huang, G., Hu, B., Song, Y., and Shi, Y. (2011). A soluble thymic stromal lymphopoietin (TSLP) antagonist, TSLPR-immunoglobulin, reduces the severity of allergic disease by regulating pulmonary dendritic cells. Clin Exp Immunol 164, 256-264.

Ziegler, S. F. (2010). The role of thymic stromal lymphopoietin (TSLP) in allergic disorders. Current opinion in immunology 22, 795-799.

Ziegler, S. F. (2012). Thymic stromal lymphopoietin and allergic disease. J Allergy Clin Immunol 130, 845-852.

Ziegler, S. F., and Artis, D. (2010). Sensing the outside world: TSLP regulates barrier immunity. Nat Immunol 11, 289-293.

Ziegler, S. F., Roan, F., Bell, B. D., Stoklasek, T. A., Kitajima, M., and Han, H. (2013). The biology of thymic stromal lymphopoietin (TSLP). Advances in pharmacology 66, 129-155.

---

The invention claimed is:

1. A monomeric fusion protein comprising:
an extracellular part of the thymic stromal lymphopoietin receptor (TSLPR) comprising an amino acid sequence having at least 80% sequence identity with the amino acid sequence of SEQ ID NO: 1; and
an extracellular part of the interleukin-7 receptor alpha (IL-7Ralpha) comprising an amino acid sequence having at least 80% sequence identity with the amino acid sequence of SEQ ID NO: 2;
wherein the monomeric fusion protein is not an Fc fusion protein; and
wherein the monomeric fusion protein binds thymic stromal lymphopoietin.

2. The monomeric fusion protein of claim 1, wherein the extracellular part of the TSLPR and the extracellular part of the IL-7Ralpha are connected by a linker.

3. The monomeric fusion protein of claim 2, wherein the linker comprises at least 10 amino acids.

4. The monomeric fusion protein of claim 2, wherein the linker is a GGS linker consisting of 5 to 20 GGS units.

5. The monomeric fusion protein of claim 1, wherein the fusion protein comprises the amino acid sequence of SEQ ID NO: 1 and the amino acid sequence of SEQ ID NO: 2.

6. A medicament comprising the monomeric fusion protein of claim 1.

7. A pharmaceutical composition comprising the monomeric fusion protein of claim 1 and a pharmaceutically acceptable carrier.

8. The monomeric fusion protein of claim 1,
wherein the extracellular part of TSLPR comprises an amino acid sequence having at least 90% sequence identity with the amino acid sequence of SEQ ID NO: 1; and
wherein the extracellular part of IL-7Ralpha comprises an amino acid sequence having at least 90% sequence identity with the amino acid sequence of SEQ ID NO: 2.

9. The monomeric fusion protein of claim 1,
wherein the extracellular part of TSLPR comprises an amino acid sequence having at least 95% sequence identity with the amino acid sequence of SEQ ID NO: 1; and
wherein the extracellular part of IL-7Ralpha comprises an amino acid sequence having at least 95% sequence identity with the amino acid sequence of SEQ ID NO: 2.

10. A nucleic acid encoding at least the fusion protein of claim 1.

11. A host cell comprising the nucleic acid of claim 10.

12. A method for the production of a fusion protein, the method comprising:
producing the fusion protein in the host cell of claim 11.

13. A method of providing a fusion protein to a subject, the method comprising: administering to the subject the monomeric fusion protein of claim 1.

14. The method according to claim 13, wherein the administration of the fusion protein treats asthma, and/or atopic dermatitis in the subject.

15. A single polypeptide strand comprising:
an amino acid sequence having at least 90% identity to SEQ ID NO: 1; and
an amino acid sequence having at least 90% identity to SEQ ID NO: 2
wherein the single polypeptide strand is not an Fc fusion protein; and
wherein the single polypeptide strand binds thymic stromal lymphopoietin.

16. A method of providing a fusion protein to a subject, the method comprising: administering to the subject the monomeric fusion protein of claim 15.

17. The method according to claim 16, wherein the administration of the fusion protein treats asthma and/or atopic dermatitis in the subject.

* * * * *

SEQUENCE LISTING

<160> NUMBER OF SEQ ID NOS: 8

<210> SEQ ID NO 1
<211> LENGTH: 183
<212> TYPE: PRT
<213> ORGANISM: Homo sapiens

<400> SEQUENCE: 1

```
Gly Val Gln Ile Gln Ile Ile Tyr Phe Asn Leu Glu Thr Val Gln Val
1               5                   10                  15

Thr Trp Asn Ala Ser Lys Tyr Ser Arg Thr Asn Leu Thr Phe His Tyr
            20                  25                  30

Arg Phe Asn Gly Asp Glu Ala Tyr Asp Gln Cys Thr Asn Tyr Leu Leu
        35                  40                  45

Gln Glu Gly His Thr Ser Gly Cys Leu Leu Asp Ala Glu Gln Arg Asp
    50                  55                  60

Asp Ile Leu Tyr Phe Ser Ile Arg Asn Gly Thr His Pro Val Phe Thr
65                  70                  75                  80

Ala Ser Arg Trp Met Val Tyr Tyr Leu Lys Pro Ser Ser Pro Lys His
                85                  90                  95

Val Arg Phe Ser Trp His Gln Asp Ala Val Thr Val Thr Cys Ser Asp
            100                 105                 110

Leu Ser Tyr Gly Asp Leu Leu Tyr Glu Val Gln Tyr Arg Ser Pro Phe
        115                 120                 125

Asp Thr Glu Trp Gln Ser Lys Gln Glu Asn Thr Cys Asn Val Thr Ile
    130                 135                 140

Glu Gly Leu Asp Ala Glu Lys Cys Tyr Ser Phe Trp Val Arg Val Lys
145                 150                 155                 160

Ala Met Glu Asp Val Tyr Gly Pro Asp Thr Tyr Pro Ser Asp Trp Ser
                165                 170                 175

Glu Val Thr Cys Trp Gln Arg
            180
```

<210> SEQ ID NO 2
<211> LENGTH: 192
<212> TYPE: PRT
<213> ORGANISM: Homo sapiens

<400> SEQUENCE: 2

```
Tyr Ser Phe Ser Cys Tyr Ser Gln Leu Glu Val Asn Gly Ser Gln His
1               5                   10                  15

Ser Leu Thr Cys Ala Phe Glu Asp Pro Asp Val Asn Thr Thr Asn Leu
            20                  25                  30

Glu Phe Glu Ile Cys Gly Ala Leu Val Glu Val Lys Cys Leu Asn Phe
        35                  40                  45

Arg Lys Leu Gln Glu Ile Tyr Phe Ile Glu Thr Lys Lys Phe Leu Leu
    50                  55                  60

Ile Gly Lys Ser Asn Ile Cys Val Lys Val Gly Glu Lys Ser Leu Thr
```

```
              65                   70                  75                  80
Cys Lys Lys Ile Asp Leu Thr Thr Ile Val Lys Pro Glu Ala Pro Phe
                    85                  90                  95

Asp Leu Ser Val Ile Tyr Arg Glu Gly Ala Asn Asp Phe Val Val Thr
                100                 105                 110

Phe Asn Thr Ser His Leu Gln Lys Lys Tyr Val Lys Val Leu Met His
                115                 120                 125

Asp Val Ala Tyr Arg Gln Glu Lys Asp Glu Asn Lys Trp Thr His Val
                130                 135                 140

Asn Leu Ser Ser Thr Lys Leu Thr Leu Leu Gln Arg Lys Leu Gln Pro
145                 150                 155                 160

Ala Ala Met Tyr Glu Ile Lys Val Arg Ser Ile Pro Asp His Tyr Phe
                165                 170                 175

Lys Gly Phe Trp Ser Glu Trp Ser Pro Ser Tyr Tyr Phe Arg Thr Pro
                180                 185                 190

<210> SEQ ID NO 3
<211> LENGTH: 499
<212> TYPE: PRT
<213> ORGANISM: Homo sapiens

<400> SEQUENCE: 3

Gly Ala Ala Glu Gly Val Gln Ile Gln Ile Ile Tyr Phe Asn Leu Glu
1               5                   10                  15

Thr Val Gln Val Thr Trp Asn Ala Ser Lys Tyr Ser Arg Thr Asn Leu
                20                  25                  30

Thr Phe His Tyr Arg Phe Asn Gly Asp Glu Ala Tyr Asp Gln Cys Thr
                35                  40                  45

Asn Tyr Leu Leu Gln Glu Gly His Thr Ser Gly Cys Leu Leu Asp Ala
                50                  55                  60

Glu Gln Arg Asp Asp Ile Leu Tyr Phe Ser Ile Arg Asn Gly Thr His
65                  70                  75                  80

Pro Val Phe Thr Ala Ser Arg Trp Met Val Tyr Tyr Leu Lys Pro Ser
                85                  90                  95

Ser Pro Lys His Val Arg Phe Ser Trp His Gln Asp Ala Val Thr Val
                100                 105                 110

Thr Cys Ser Asp Leu Ser Tyr Gly Asp Leu Leu Tyr Glu Val Gln Tyr
                115                 120                 125

Arg Ser Pro Phe Asp Thr Glu Trp Gln Ser Lys Gln Glu Asn Thr Cys
                130                 135                 140

Asn Val Thr Ile Glu Gly Leu Asp Ala Glu Lys Cys Tyr Ser Phe Trp
145                 150                 155                 160

Val Arg Val Lys Ala Met Glu Asp Val Tyr Gly Pro Asp Thr Tyr Pro
                165                 170                 175

Ser Asp Trp Ser Glu Val Thr Cys Trp Gln Arg Gly Glu Ile Arg Asp
                180                 185                 190

Ala Cys Ala Glu Thr Pro Thr Pro Pro Lys Pro Lys Leu Ser Lys Ser
                195                 200                 205

Arg Gly Gly Ser Gly Gly Ser Gly Gly Ser Gly Gly Ser Gly Gly Ser
                210                 215                 220

Gly Gly Ser Gly Gly Ser Gly Gly Ser Gly Gly Ser Gly Gly Ser Gly
225                 230                 235                 240

Gly Ser Gly Gly Ser Gly Gly Ser Gly Gly Ser Gly Gly Ser Gly Gly
                245                 250                 255
```

Ser Gly Gly Ser Gly Gly Ser Gly Gly Ser Gly Gly Ser Leu Gln Glu
            260                 265                 270

Ser Gly Tyr Ala Gln Asn Gly Asp Leu Glu Asp Ala Glu Leu Asp Asp
            275                 280                 285

Tyr Ser Phe Ser Cys Tyr Ser Gln Leu Glu Val Asn Gly Ser Gln His
            290                 295                 300

Ser Leu Thr Cys Ala Phe Glu Asp Pro Asp Val Asn Thr Thr Asn Leu
305                 310                 315                 320

Glu Phe Glu Ile Cys Gly Ala Leu Val Glu Val Lys Cys Leu Asn Phe
                    325                 330                 335

Arg Lys Leu Gln Glu Ile Tyr Phe Ile Glu Thr Lys Lys Phe Leu Leu
            340                 345                 350

Ile Gly Lys Ser Asn Ile Cys Val Lys Val Gly Glu Lys Ser Leu Thr
            355                 360                 365

Cys Lys Lys Ile Asp Leu Thr Thr Ile Val Lys Pro Glu Ala Pro Phe
            370                 375                 380

Asp Leu Ser Val Ile Tyr Arg Glu Gly Ala Asn Asp Phe Val Val Thr
385                 390                 395                 400

Phe Asn Thr Ser His Leu Gln Lys Lys Tyr Val Lys Val Leu Met His
                    405                 410                 415

Asp Val Ala Tyr Arg Gln Glu Lys Asp Glu Asn Lys Trp Thr His Val
            420                 425                 430

Asn Leu Ser Ser Thr Lys Leu Thr Leu Leu Gln Arg Lys Leu Gln Pro
            435                 440                 445

Ala Ala Met Tyr Glu Ile Lys Val Arg Ser Ile Pro Asp His Tyr Phe
            450                 455                 460

Lys Gly Phe Trp Ser Glu Trp Ser Pro Ser Tyr Tyr Phe Arg Thr Pro
465                 470                 475                 480

Glu Ile Asn Asn Ser Ser Gly Glu Met Asp Gly Thr Lys His His His
                    485                 490                 495

His His His

<210> SEQ ID NO 4
<211> LENGTH: 504
<212> TYPE: PRT
<213> ORGANISM: Homo sapiens

<400> SEQUENCE: 4

Glu Thr Gly Glu Ser Gly Tyr Ala Gln Asn Gly Asp Leu Glu Asp Ala
1               5                   10                  15

Glu Leu Asp Asp Tyr Ser Phe Ser Cys Tyr Ser Gln Leu Glu Val Asn
            20                  25                  30

Gly Ser Gln His Ser Leu Thr Cys Ala Phe Glu Asp Pro Asp Val Asn
        35                  40                  45

Thr Thr Asn Leu Glu Phe Glu Ile Cys Gly Ala Leu Val Glu Val Lys
    50                  55                  60

Cys Leu Asn Phe Arg Lys Leu Gln Glu Ile Tyr Phe Ile Glu Thr Lys
65                  70                  75                  80

Lys Phe Leu Leu Ile Gly Lys Ser Asn Ile Cys Val Lys Val Gly Glu
                85                  90                  95

Lys Ser Leu Thr Cys Lys Lys Ile Asp Leu Thr Thr Ile Val Lys Pro
            100                 105                 110

Glu Ala Pro Phe Asp Leu Ser Val Ile Tyr Arg Glu Gly Ala Asn Asp
        115                 120                 125

```
Phe Val Val Thr Phe Asn Thr Ser His Leu Gln Lys Lys Tyr Val Lys
            130                 135                 140

Val Leu Met His Asp Val Ala Tyr Arg Gln Glu Lys Asp Glu Asn Lys
145                 150                 155                 160

Trp Thr His Val Asn Leu Ser Ser Thr Lys Leu Thr Leu Leu Gln Arg
                165                 170                 175

Lys Leu Gln Pro Ala Ala Met Tyr Glu Ile Lys Val Arg Ser Ile Pro
            180                 185                 190

Asp His Tyr Phe Lys Gly Phe Trp Ser Glu Trp Ser Pro Ser Tyr Tyr
            195                 200                 205

Phe Arg Thr Pro Glu Ile Asn Asn Ser Ser Gly Glu Met Asp Ser Arg
210                 215                 220

Gly Gly Ser Gly Gly Ser Gly Gly Ser Gly Gly Ser Gly Gly Ser Gly
225                 230                 235                 240

Gly Ser Gly Gly Ser Gly Gly Ser Gly Gly Ser Gly Gly Ser Gly Gly
                245                 250                 255

Ser Gly Gly Ser Gly Gly Ser Gly Gly Ser Gly Gly Ser Gly Gly Ser
            260                 265                 270

Gly Gly Ser Gly Gly Ser Gly Gly Ser Gly Gly Ser Leu Gln Gln Gly
            275                 280                 285

Gly Ala Ala Glu Gly Val Gln Ile Gln Ile Ile Tyr Phe Asn Leu Glu
            290                 295                 300

Thr Val Gln Val Thr Trp Asn Ala Ser Lys Tyr Ser Arg Thr Asn Leu
305                 310                 315                 320

Thr Phe His Tyr Arg Phe Asn Gly Asp Glu Ala Tyr Asp Gln Cys Thr
                325                 330                 335

Asn Tyr Leu Leu Gln Glu Gly His Thr Ser Gly Cys Leu Leu Asp Ala
            340                 345                 350

Glu Gln Arg Asp Asp Ile Leu Tyr Phe Ser Ile Arg Asn Gly Thr His
            355                 360                 365

Pro Val Phe Thr Ala Ser Arg Trp Met Val Tyr Leu Lys Pro Ser
            370                 375                 380

Ser Pro Lys His Val Arg Phe Ser Trp His Gln Asp Ala Val Thr Val
385                 390                 395                 400

Thr Cys Ser Asp Leu Ser Tyr Gly Asp Leu Leu Tyr Glu Val Gln Tyr
                405                 410                 415

Arg Ser Pro Phe Asp Thr Glu Trp Gln Ser Lys Gln Glu Asn Thr Cys
            420                 425                 430

Asn Val Thr Ile Glu Gly Leu Asp Ala Glu Lys Cys Tyr Ser Phe Trp
            435                 440                 445

Val Arg Val Lys Ala Met Glu Asp Val Tyr Gly Pro Asp Thr Tyr Pro
450                 455                 460

Ser Asp Trp Ser Glu Val Thr Cys Trp Gln Arg Gly Glu Ile Arg Asp
465                 470                 475                 480

Ala Cys Ala Glu Thr Pro Thr Pro Pro Lys Pro Lys Leu Ser Lys Gly
            485                 490                 495

Thr Lys His His His His His His
            500

<210> SEQ ID NO 5
<211> LENGTH: 24
<212> TYPE: PRT
<213> ORGANISM: Homo sapiens

<400> SEQUENCE: 5
```

```
Met Gly Arg Leu Val Leu Leu Trp Gly Ala Ala Val Phe Leu Leu Gly
1               5                   10                  15

Gly Trp Met Ala Leu Gly Gln Gly
            20

<210> SEQ ID NO 6
<211> LENGTH: 28
<212> TYPE: PRT
<213> ORGANISM: Artificial Sequence
<220> FEATURE:
<223> OTHER INFORMATION: secretion signal of the pHLsec-vector

<400> SEQUENCE: 6

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala
            20                  25

<210> SEQ ID NO 7
<211> LENGTH: 207
<212> TYPE: PRT
<213> ORGANISM: Homo sapiens

<400> SEQUENCE: 7

Gly Ala Ala Glu Gly Val Gln Ile Gln Ile Ile Tyr Phe Asn Leu Glu
1               5                   10                  15

Thr Val Gln Val Thr Trp Asn Ala Ser Lys Tyr Ser Arg Thr Asn Leu
            20                  25                  30

Thr Phe His Tyr Arg Phe Asn Gly Asp Glu Ala Tyr Asp Gln Cys Thr
        35                  40                  45

Asn Tyr Leu Leu Gln Glu Gly His Thr Ser Gly Cys Leu Leu Asp Ala
    50                  55                  60

Glu Gln Arg Asp Asp Ile Leu Tyr Phe Ser Ile Arg Asn Gly Thr His
65                  70                  75                  80

Pro Val Phe Thr Ala Ser Arg Trp Met Val Tyr Tyr Leu Lys Pro Ser
                85                  90                  95

Ser Pro Lys His Val Arg Phe Ser Trp His Gln Asp Ala Val Thr Val
            100                 105                 110

Thr Cys Ser Asp Leu Ser Tyr Gly Asp Leu Leu Tyr Glu Val Gln Tyr
        115                 120                 125

Arg Ser Pro Phe Asp Thr Glu Trp Gln Ser Lys Gln Glu Asn Thr Cys
    130                 135                 140

Asn Val Thr Ile Glu Gly Leu Asp Ala Glu Lys Cys Tyr Ser Phe Trp
145                 150                 155                 160

Val Arg Val Lys Ala Met Glu Asp Val Tyr Gly Pro Asp Thr Tyr Pro
                165                 170                 175

Ser Asp Trp Ser Glu Val Thr Cys Trp Gln Arg Gly Glu Ile Arg Asp
            180                 185                 190

Ala Cys Ala Glu Thr Pro Thr Pro Lys Pro Lys Leu Ser Lys
        195                 200                 205

<210> SEQ ID NO 8
<211> LENGTH: 219
<212> TYPE: PRT
<213> ORGANISM: Homo sapiens

<400> SEQUENCE: 8

Glu Ser Gly Tyr Ala Gln Asn Gly Asp Leu Glu Asp Ala Glu Leu Asp
```

```
1               5                    10                   15
Asp Tyr Ser Phe Ser Cys Tyr Ser Gln Leu Glu Val Asn Gly Ser Gln
            20                  25                  30

His Ser Leu Thr Cys Ala Phe Glu Asp Pro Asp Val Asn Thr Thr Asn
            35                  40                  45

Leu Glu Phe Glu Ile Cys Gly Ala Leu Val Glu Val Lys Cys Leu Asn
            50                  55                  60

Phe Arg Lys Leu Gln Glu Ile Tyr Phe Ile Glu Thr Lys Lys Phe Leu
65                  70                  75                  80

Leu Ile Gly Lys Ser Asn Ile Cys Val Lys Val Gly Glu Lys Ser Leu
                85                  90                  95

Thr Cys Lys Lys Ile Asp Leu Thr Thr Ile Val Lys Pro Glu Ala Pro
            100                 105                 110

Phe Asp Leu Ser Val Ile Tyr Arg Glu Gly Ala Asn Asp Phe Val Val
            115                 120                 125

Thr Phe Asn Thr Ser His Leu Gln Lys Lys Tyr Val Lys Val Leu Met
            130                 135                 140

His Asp Val Ala Tyr Arg Gln Glu Lys Asp Glu Asn Lys Trp Thr His
145                 150                 155                 160

Val Asn Leu Ser Ser Thr Lys Leu Thr Leu Leu Gln Arg Lys Leu Gln
                165                 170                 175

Pro Ala Ala Met Tyr Glu Ile Lys Val Arg Ser Ile Pro Asp His Tyr
            180                 185                 190

Phe Lys Gly Phe Trp Ser Glu Trp Ser Pro Ser Tyr Tyr Phe Arg Thr
            195                 200                 205

Pro Glu Ile Asn Asn Ser Ser Gly Glu Met Asp
            210                 215
```